(12) United States Patent
Curro et al.

(10) Patent No.: US 10,011,953 B2
(45) Date of Patent: *Jul. 3, 2018

(54) BULKED ABSORBENT MEMBERS

(75) Inventors: John Joseph Curro, Cincinnati, OH (US); Jill Marlene Orr, Liberty Township, OH (US); Keith Robert Priessman, Hamilton, OH (US); John Brian Strube, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 874 days.

This patent is subject to a terminal disclaimer.

(21) Appl. No.: 13/455,508

(22) Filed: Apr. 25, 2012

(65) Prior Publication Data
US 2012/0273146 A1 Nov. 1, 2012

Related U.S. Application Data

(63) Continuation-in-part of application No. 13/094,195, filed on Apr. 26, 2011, now Pat. No. 8,657,596, and
(Continued)

(51) Int. Cl.
*D21H 27/02* (2006.01)
*D21H 27/00* (2006.01)
(Continued)

(52) U.S. Cl.
CPC ........... *D21H 27/002* (2013.01); *D21H 27/02* (2013.01); *A61F 13/00* (2013.01);
(Continued)

(58) Field of Classification Search
CPC . B32B 3/28; B32B 3/30; D21H 27/02; D21H 27/002; A61F 13/00;
(Continued)

(56) References Cited

U.S. PATENT DOCUMENTS 3,017,304 A 1/1962 Burgeni
3,496,259 A 2/1970 Guenther
(Continued)

FOREIGN PATENT DOCUMENTS

EP 0598970 B2 6/1994
EP 0959164 11/1999
(Continued)

OTHER PUBLICATIONS

U.S. Appl. No. 13/094,477, filed Apr. 26, 2011, Keith Joseph Stone et al.
(Continued)

*Primary Examiner* — Donald J Loney
(74) *Attorney, Agent, or Firm* — Christian M. Best; Charles R. Ware

(57) ABSTRACT

Absorbent members, especially bulked absorbent members, and methods of making the same are disclosed. The absorbent member may be in the form of a unitary absorbent fibrous layer comprising at least some cellulose fibers. The unitary absorbent fibrous layer is at least partially stratified through its thickness. The absorbent member may also have a plurality of discrete deformations, such as depressions and/or apertures in its surfaces. The method involves subjecting a precursor web to at least one cycle (or pass) through a mechanical deformation process. The mechanical deformation process utilizes a first forming member and a second forming member that form a nip therebetween through which the precursor web is passed. The first and second forming members are moving at different speeds relative to each other when they come together to form the nip.

19 Claims, 14 Drawing Sheets

Related U.S. Application Data a continuation-in-part of application No. 13/094,295, filed on Apr. 26, 2011.

(51) Int. Cl.
|  |  |
|---|---|
| B32B 3/30 | (2006.01) |
| A61F 13/511 | (2006.01) |
| A61F 13/00 | (2006.01) |
| B32B 3/28 | (2006.01) |

(52) U.S. Cl.
CPC .......... *A61F 13/51104* (2013.01); *B32B 3/28* (2013.01); *B32B 3/30* (2013.01); *Y10T 428/24322* (2015.01); *Y10T 428/24612* (2015.01); *Y10T 428/24942* (2015.01)

(58) Field of Classification Search
CPC ....... A61F 13/51104; Y10T 428/24322; Y10T 428/24612; Y10T 428/24942
See application file for complete search history.

(56) References Cited

U.S. PATENT DOCUMENTS

| | | |
|---|---|---|
| 3,509,007 A | 4/1970 | Kalwaites |
| 3,994,771 A | 11/1976 | Morgan, Jr. et al. |
| 4,189,344 A | 2/1980 | Busker |
| 4,300,981 A | 11/1981 | Carstens |
| 4,355,066 A * | 10/1982 | Newman ............. A47K 10/16 15/209.1 |
| 4,432,833 A | 2/1984 | Breese |
| 4,559,050 A | 12/1985 | Iskra |
| 4,596,567 A * | 6/1986 | Iskra ............. A61F 13/15203 604/368 |
| 4,761,322 A | 8/1988 | Raley |
| 4,818,315 A | 4/1989 | Hellgren et al. |
| 4,992,324 A | 2/1991 | Dube |
| 5,143,679 A | 9/1992 | Weber |
| 5,167,897 A | 12/1992 | Weber et al. |
| 5,242,435 A | 9/1993 | Murji et al. |
| 5,356,403 A | 10/1994 | Faulks et al. |
| 5,387,385 A | 2/1995 | Murji et al. |
| 5,399,175 A | 3/1995 | Glaug et al. |
| 5,455,992 A | 10/1995 | Kurschatke et al. |
| 5,462,537 A | 10/1995 | Carr et al. |
| 5,518,801 A | 5/1996 | Chappell et al. |
| 5,562,645 A | 10/1996 | Tanzer et al. |
| 5,634,915 A * | 6/1997 | Osterdahl ............. A61F 13/15 604/367 |
| 5,641,441 A | 6/1997 | Yang |
| 5,691,035 A | 11/1997 | Chappell et al. |
| 5,704,101 A | 1/1998 | Majors et al. |
| 5,723,087 A | 3/1998 | Chappell et al. |
| 5,743,999 A | 4/1998 | Kamps |
| 5,891,544 A | 4/1999 | Chappell et al. |
| 5,916,507 A | 6/1999 | Dabi et al. |
| 5,916,663 A | 6/1999 | Chappell et al. |
| 5,919,178 A | 7/1999 | Widlund |
| 5,925,299 A | 7/1999 | Dierckes et al. |
| 5,990,377 A | 11/1999 | Chen et al. |
| 6,007,468 A | 12/1999 | Giacometti |
| 6,027,483 A | 2/2000 | Chappell et al. |
| 6,053,232 A | 4/2000 | Biagiotti |
| 6,074,524 A | 6/2000 | Wu et al. |
| 6,077,526 A | 6/2000 | Scully et al. |
| 6,177,605 B1 | 1/2001 | Trombetta et al. |
| 6,203,654 B1 | 3/2001 | McFall et al. |
| 6,264,872 B1 | 7/2001 | Majors et al. |
| 6,296,737 B1 | 10/2001 | Wu et al. |
| 6,344,109 B1 | 2/2002 | Gross |
| 6,344,111 B1 | 2/2002 | Wilhelm |
| 6,355,200 B1 | 3/2002 | Schmidt et al. |
| 6,458,447 B1 | 10/2002 | Cabell et al. |
| 6,521,812 B1 * | 2/2003 | Graef ............. A61F 13/531 604/375 |
| 6,533,898 B2 | 3/2003 | Gross |
| 6,608,236 B1 | 8/2003 | Hetzler et al. |
| 6,610,390 B1 * | 8/2003 | Kauschke ............. B32B 5/26 428/198 |
| 6,630,054 B1 * | 10/2003 | Graef ............. A61F 13/15617 162/101 |
| 6,642,432 B1 | 11/2003 | Matsui et al. |
| 6,739,024 B1 | 5/2004 | Wagner |
| 6,913,718 B2 | 7/2005 | Ducker et al. |
| 7,081,559 B2 | 7/2006 | Fujikawa et al. |
| 7,112,257 B2 | 9/2006 | Baggot et al. |
| 7,497,926 B2 | 3/2009 | Hermans et al. |
| 7,527,615 B2 | 5/2009 | Roe et al. |
| 7,632,979 B2 | 12/2009 | Fujii et al. |
| 7,772,457 B2 | 8/2010 | Ohtsuka et al. |
| 7,935,207 B2 | 5/2011 | Zhao et al. |
| 8,021,591 B2 | 9/2011 | Curro et al. |
| 8,502,013 B2 | 8/2013 | Zhao et al. |
| 2002/0177827 A1 | 11/2002 | Noda et al. |
| 2003/0121380 A1 | 7/2003 | Cowell et al. |
| 2003/0204178 A1 | 10/2003 | Febo et al. |
| 2004/0049166 A1 | 3/2004 | Chen et al. |
| 2004/0253894 A1 * | 12/2004 | Fell ............. A61F 13/15707 442/381 |
| 2005/0021753 A1 | 1/2005 | Coleman |
| 2005/0064136 A1 | 3/2005 | Turner et al. |
| 2005/0112979 A1 | 5/2005 | Sawyer et al. |
| 2005/0173085 A1 | 8/2005 | Schulz |
| 2005/0217814 A1 | 10/2005 | Super et al. |
| 2006/0087053 A1 | 4/2006 | Turner et al. |
| 2006/0128247 A1 | 6/2006 | Skoog et al. |
| 2006/0151914 A1 | 7/2006 | Gerndt |
| 2006/0206072 A1 | 9/2006 | Malakouti et al. |
| 2006/0286343 A1 | 12/2006 | Curro et al. |
| 2008/0167634 A1 | 7/2008 | Kouta et al. |
| 2008/0217809 A1 | 9/2008 | Zhao et al. |
| 2008/0221538 A1 | 9/2008 | Zhao et al. |
| 2008/0221539 A1 | 9/2008 | Zhao et al. |
| 2008/0221541 A1 | 9/2008 | Lavash et al. |
| 2008/0221542 A1 | 9/2008 | Zhao et al. |
| 2009/0087636 A1 | 4/2009 | Yasuda et al. |
| 2010/0036343 A1 | 2/2010 | Hernandez |
| 2010/0048072 A1 * | 2/2010 | Kauschke ............. A47L 13/16 442/1 |
| 2010/0201024 A1 | 8/2010 | Gibson et al. |
| 2010/0203306 A1 * | 8/2010 | Fingal ............. A47L 13/17 428/219 |
| 2010/0318047 A1 | 12/2010 | Ducker et al. |
| 2012/0064280 A1 | 3/2012 | Hammons et al. |
| 2012/0064298 A1 | 3/2012 | Orr et al. |
| 2012/0273146 A1 | 11/2012 | Curro et al. |
| 2012/0273148 A1 | 11/2012 | Orr et al. |
| 2012/0273997 A1 | 11/2012 | Stone et al. |
| 2012/0276238 A1 | 11/2012 | Strube et al. |
| 2012/0276239 A1 | 11/2012 | Coe et al. |
| 2012/0276337 A1 | 11/2012 | Curro et al. |
| 2012/0276341 A1 | 11/2012 | Lake et al. |
| 2012/0277393 A1 | 11/2012 | Curro et al. |
| 2012/0277701 A1 | 11/2012 | Stone et al. |
| 2012/0277704 A1 | 11/2012 | Marinelli et al. |
| 2012/0277705 A1 | 11/2012 | Marinelli et al. |
| 2012/0277706 A1 | 11/2012 | Marinelli et al. |
| 2012/0277707 A1 | 11/2012 | Orr et al. |
| 2012/0277708 A1 | 11/2012 | Marinelli et al. |
| 2012/0277709 A1 | 11/2012 | Marinelli et al. |
| 2012/0277710 A1 | 11/2012 | Marinelli et al. |

FOREIGN PATENT DOCUMENTS

| | | |
|---|---|---|
| JP | H05-084262 | 4/1993 |
| JP | H10-309298 | 11/1998 |
| JP | H11-318982 | 11/1999 |
| JP | A-2006-297073 | 11/2006 |
| JP | A-2008-132055 | 6/2008 |
| JP | 2011-137248 | 7/2011 |
| WO | WO 01/85083 A1 | 11/2001 |
| WO | WO 03/041751 | 5/2003 |
| WO | WO2004/108037 A1 | 12/2004 |

(56) References Cited

FOREIGN PATENT DOCUMENTS

| WO | WO 2005/011936 A1 | 2/2005 |
|---|---|---|
| WO | WO-2005/011936 A1 | 2/2005 |
| WO | WO-2007/001270 A1 | 1/2007 |
| WO | WO2008/065628 A2 | 6/2008 |
| WO | WO-2008/107846 A1 | 9/2008 |
| WO | WO 2011/009997 A2 | 1/2011 |

OTHER PUBLICATIONS

U.S. Appl. No. 13/094,559, filed Apr. 26, 2011, Richard George Coe et al.
U.S. Appl. No. 13/094,593, filed Apr. 26, 2011, Keith Joseph Stone et al.
U.S. Appl. No. 13/094,185, filed Apr. 26, 2011, John Lee Hammons et al.
U.S. Appl. No. 13/094,195, filed Apr. 26, 2011, Kirk Wallace Lake et al.
U.S. Appl. No. 13/094,206, filed Apr. 26, 2011, Jill Marlene Orr et al.
U.S. Appl. No. 13/094,219, filed Apr. 26, 2011, John Brian Strube et al.
U.S. Appl. No. 13/094,265, filed Apr. 26, 2011, Luigi Marinelli et al.
U.S. Appl. No. 13/094,279, filed Apr. 26, 2011, Luigi Marinelli et al.
U.S. Appl. No. 13/094,295, filed Apr. 26, 2011, Luigi Marinelli et al.
U.S. Appl. No. 13/094,310, filed Apr. 26, 2011, Jill Marlene Orr et al.
U.S. Appl. No. 13/455,185, filed Apr. 25, 2012, Luigi Marinelli et al.
U.S. Appl. No. 13/455,190, filed Apr. 25, 2012, Luigi Marinelli et al.
U.S. Appl. No. 13/455,194, filed Apr. 25, 2012, Luigi Marinelli et al.
U.S. Appl. No. 13/455,199, filed Apr. 25, 2012, Jill Marlene Orr et al.
U.S. Appl. No. 13/455,532, filed Apr. 25, 2012, John Joseph Curro et al.
U.S. Appl. No. 13/455,698, filed Apr. 25, 2012, John Joseph Curro et al.
International search report dated Aug. 10, 2012, 5 pages.
International search report dated Aug. 8, 2012, 5 pages.
International search report dated Aug. 10, 2012, 6 pages.
All Office Actions, U.S. Appl. No. 13/094,265, dated Apr. 17, 2014, Jan. 2, 2015, and Apr. 24, 2015.
Office Action dated May 1, 2014, U.S. Appl. No. 13/455,185.
Office Action dated Apr. 24, 2014, U.S. Appl. No. 13/094,279.
Office Action dated Jul. 11, 2014, U.S. Appl. No. 13/455,190.
All Office Actions, U.S. Appl. No. 13/094,310.
All Office Actions, U.S. Appl. No. 13/455,194.
All Office Actions, U.S. Appl. No. 13/455,199.
All Office Actions, U.S. Appl. No. 13/094,295, including Office Action dated Feb. 25, 2016.
All Office Actions, U.S. Appl. No. 13/455,532.
PCT International Search Report, dated Aug. 21, 2012, 184 pages.
PCT International Search Report, dated Aug. 21, 2012, 234 pages.
PCT International Search Report, dated Aug. 21, 2012, 339 pages.
Russian Search Report dated Mar. 18, 2015, 2 pages.

* cited by examiner

BULKED ABSORBENT MEMBERS

CROSS REFERENCE TO RELATED APPLICATIONS

This application is a continuation-in-part of U.S. patent application Ser. Nos. 13/094,195 and 13/094,295, both filed Apr. 26, 2011.

FIELD OF THE INVENTION

The present invention is directed to absorbent members and methods of making the same, and more particularly to bulked absorbent members and methods of making the same.

BACKGROUND OF THE INVENTION

Currently, some disposable absorbent articles such as diapers, sanitary napkins, and pantiliners are provided with a low density airfelt absorbent core. Airfelt, or comminuted wood pulp, is typically made in a process that involves several steps. The first step is one in which pulp fibers are suspended in water and introduced to a moving screen from the headbox in a wetlaid paper process. The water is removed by a combination of gravity and vacuum before introduction to a drying process to form a relatively high basis weight material that is referred to as "drylap". Drylap may be in sheet or roll form. Thereafter, the drylap is shipped to the absorbent article manufacturer. The absorbent article manufacturer subjects the drylap to comminution process or shredding to make airfelt or "fluff" via an airlaid process. This is typically done on-line in an absorbent article manufacturing line.

Airfelt has several limitations when used as an absorbent core material in disposable absorbent articles. Airfelt typically has low integrity, and is subject to bunching and roping when wet. Airfelt typically has a low density and cannot provide as much capillary work potential as a higher density material. In addition, airfelt has the same density throughout the thickness, and is not readily formed into structures having zones or layers with higher densities.

Airlaid structures are another type of absorbent material commonly used in absorbent articles. The air laying process involves the comminution or shredding of drylap to make airfelt or "fluff". Binder materials, such as latex binder, may then be added to provide strength and integrity to the material. Super-absorbent polymers are often added in the air laying process as well. Airlaid structures can be formed in a manner which does provide zones with higher densities, as in US 2003/0204178 A1, but this involves more expensive processes and materials. The air laying process is often done at an intermediate supplier, resulting in added cost for shipping the material to the converting operation. The combination of more costly materials, processing, and shipping results in a significantly more expensive material and a more complex supply chain.

Various different absorbent structures and other structures used in absorbent articles, and methods of making the same, are disclosed in the patent literature, including: U.S. Pat. No. 3,017,304, Burgeni; U.S. Pat. No. 3,509,007, Kalwaites; U.S. Pat. No. 4,189,344, Busker; U.S. Pat. No. 4,992,324, Dube; U.S. Pat. No. 5,143,679, Weber; U.S. Pat. No. 5,242,435, Murji; U.S. Pat. No. 5,518,801, Chappell, et al.; U.S. Pat. No. 5,562,645, Tanzer, et al.; U.S. Pat. No. 5,634,915, Osterhahl; U.S. Pat. No. 5,743,999, Kamps; U.S. Pat. No. 6,344,111 B1, Wilhelm; U.S. Patent Application Publication No. 2003/0204178 A1, Febo, et al.; U.S. Patent Application Publication No. 2006/0151914, Gerndt; U.S. Patent Application Publication No. 2008/0217809 A1, Zhao, et al.; U.S. Patent Application Publication No. 2008/0221538 A1, Zhao, et al.; U.S. Patent Application Publication No. 2008/0221539 A1, Zhao, et al.; U.S. Patent Application Publication No. 2008/0221541 A1, Lavash, et al.; U.S. Patent Application Publication No. 2008/0221542 A1, Zhao, et al.; U.S. Patent Application Publication No. 2010/0318047 A1, Ducker, et al.; and, EP 0 598 970 B2. However, the search for improved absorbent structures and methods of making the same has continued.

It is desirable to provide improved absorbent members and methods of making the same. In particular, it is desirable to provide absorbent members with improved liquid acquisition, flexibility, tensile strength, and fluid retention. Ideally, it is desirable to produce such improved absorbent members at a low cost.

SUMMARY OF THE INVENTION

The present invention is directed to absorbent members and methods of making the same, and more particularly to bulked absorbent members and methods of making the same.

The absorbent member comprises at least one unitary absorbent fibrous layer or web comprising at least some cellulose fibers. The fibrous layer has a first surface, a second surface, a length, a width, and a thickness. The unitary absorbent fibrous layer is at least partially stratified through its thickness. The absorbent member may also have a plurality of discrete deformations in its first and second surfaces. Other optional features are possible. For example, the absorbent members described above can be further compacted in regions, or over their entire surface. In other embodiments, the absorbent members can be provided with a three-dimensional topography. In still other embodiments, the absorbent members can be apertured.

The methods of forming the absorbent members involve subjecting a precursor web to at least one cycle (or pass) through a mechanical deformation process. The precursor material may be in roll or sheet form (e.g., sheet pulp). The precursor material may comprise any suitable wet laid cellulose-containing material, including but not limited to: drylap, liner board, paper board, post-consumer recycled material, filter paper, and combinations thereof. The methods involve passing the precursor web through a pair of forming members which may include, but are not limited to counter-rotating rolls. Typically, the methods involve subjecting the precursor web to at least one pass through the nip between counter-rotating rolls that are rotating at different surface speeds. The rolls comprise a first roll having a surface comprising a plurality of first forming elements, wherein said first forming elements comprise discrete male forming elements; and a second roll having a surface comprising a plurality of second forming elements, wherein said second forming elements comprise discrete male forming elements.

Optionally, the methods may also involve subjecting the precursor web to multiple cycles (or passes) through an additional mechanical deformation process. The additional mechanical deformation process may utilize forming members that include, but are not limited to counter-rotating rolls that are rotating at substantially the same surface speeds. The surface of the individual rolls in the additional deformation process may, depending on the desired type of deformation, be: smooth (i.e., an anvil roll); or, provided with forming elements comprising protrusions or "male" elements. The multiple cycles of the optional mechanical deformation process may utilize a "nested" roll arrangement in which there are at least four rolls and at least two of the rolls define two or more nips with the other rolls.

The methods described herein may be used for a variety of purposes. Such purposes can range from serving as a pre-processing step prior to feeding the precursor material into a hammer mill in order to reduce the energy required to defibrillate the material in the hammer mill, to serving as a unit operation in an absorbent article manufacturing line in order to prepare a completed absorbent member that is ready for use in an absorbent article being made on the line.

BRIEF DESCRIPTION OF THE DRAWINGS

The following detailed description will be more fully understood in view of the drawings in which.

Figure 1:
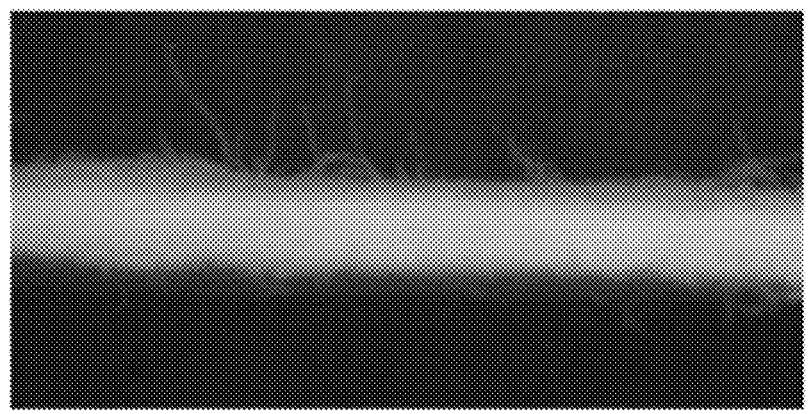
FIG. 1 is a photomicrograph of the cross-section of a web of dry lap.

The embodiments of the absorbent structure and methods of making the same shown in the drawings are illustrative in nature and are not intended to be limiting of the invention defined by the claims. Moreover, the features of the invention will be more fully apparent and understood in view of the detailed description.

DETAILED DESCRIPTION

Definitions

The term "absorbent article" includes disposable articles such as sanitary napkins, panty liners, tampons, interlabial devices, wound dressings, diapers, adult incontinence articles, wipes, and the like. Still further, the absorbent members produced by the methods and apparatuses disclosed herein can find utility in other webs such as scouring pads, dry-mop pads (such as SWIFFER® pads), and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. Various absorbent articles described above will typically comprise a liquid pervious topsheet, a liquid impervious backsheet joined to the topsheet, and an absorbent core between the topsheet and backsheet.

The term "absorbent core", as used herein, refers to the component of the absorbent article that is primarily responsible for storing liquids. As such, the absorbent core typically does not include the topsheet or backsheet of the absorbent article.

The term "absorbent member", as used herein, refers to the components of the absorbent article that typically provide one or more liquid handling functionality, e.g., liquid acquisition, liquid distribution, liquid transportation, liquid storage, etc. If the absorbent member comprises an absorbent core component, the absorbent member can comprise the entire absorbent core or only a portion of the absorbent core.

The terms "compaction" and "re-densification", as used herein, refer to a process step in which the bulk density of a web is increased.

The term "cross-machine direction" (or "cross direction") refers to a direction that is perpendicular to the machine direction in the plane of the web.

The term "de-densification", as used herein, refers to a "density reduction" in which the bulk density of a web is reduced.

The term "density profile", as used herein, refers to a change in density through the thickness of an absorbent member, and is distinguishable from ordinary variations in the density of absorbent members having a substantially uniform density throughout the thickness. The density profile can be in any of the configurations described herein. Density profiles may be illustrated in photomicrographs and SEMs.

The term "discrete", as used herein, means distinct or unconnected. When the term "discrete" is used relative to forming elements on a forming member, it is meant that the distal (or radially outwardmost) ends of the forming elements are distinct or unconnected in both the machine direction and cross-machine direction (even though bases of the forming elements may be formed into the same surface of a roll, for example). For example, the ridges on a ring roll are not considered to be discrete.

The term "disposable" is used herein to describe absorbent articles which are not intended to be laundered or otherwise restored or reused as an absorbent article (i.e., they are intended to be discarded after use and, preferably, to be recycled, composted or otherwise disposed of in an environmentally compatible manner).

The term "drylap", as used herein, refers to a dried, wetlaid cellulose-containing fibrous material that may be in roll or sheet form. Drylap is also known as fluff pulp or combination pulp. For some applications, drylap comprises SBSK (Southern Bleached Softwood Kraft) or NBSK (Northern Bleached Softwood Kraft) pulp produced in relatively heavy caliper, high basis weight sheet form. The sheet product is rewound into continuous rolls or stacks of sheets for shipment to a disposable article manufacturer. At the manufacturer's plant, the rolls are continuously fed into a device, such as a hammermill, to be reduced as much as reasonably possible to individual fibers thereby creating cellulose "fluff". Alternatively, drylap grades of material can be de-densified by the processes described herein. In addition to cellulose fibers, drylap can include fibers of rayon, polyester, cotton, post-consumer recycled material, other fibrous materials, or even particulate additives comprising items such as mineral fillers, Kaolin clay, or powdered cellulose. Drylap materials of the type useful in this invention include those described in U.S. Pat. Nos. 6,074,524 and 6,296,737.

The terms "exterior", "outer", and "outside", as used herein with reference to zones of an absorbent member, refer to those zones that are spaced in the z-direction away from a plane that runs through the center of the absorbent member.

The term "machine direction" means the path that material, such as a web, follows through a manufacturing process.

The terms "mechanically impacting" or "mechanically deforming", may be used interchangeably herein, to refer to processes in which a mechanical force is exerted upon a material.

The term "Micro-SELF" is a process that is similar in apparatus and method to that of the SELF process defined herein. Micro-SELF teeth have different dimensions such that they are more conducive to forming tufts with openings on the leading and trailing ends. A process using micro-SELF to form tufts in a web substrate is disclosed in U.S. Patent application Publication No. US 2006/0286343A1. For the purposes of the present disclosure, Micro-SELF will be considered to be a subset of SELF technology.

The term "paper board", as used herein, refers to the class of heavyweight paper and other fiberboards thicker than 0.15 millimeter, including boxboard, cardboard, chipboard, containerboard, corrugated board, and linerboard.

The term "patterned", as used herein with reference to the forming members, includes forming members having discrete elements thereon, as well as those having continuous features thereon such as the ridges and grooves on a ring roll.

The term "post-consumer recycled material" as used herein generally refers to material that can originate from post-consumer sources such as domestic, distribution, retail, industrial, and demolition. "Post-consumer fibers" means fibers obtained from consumer products that have been discarded for disposal or recovery after having completed their intended uses and is intended to be a subset of post consumer recycled materials. Post-consumer materials may be obtained from the sorting of materials from a consumer or manufacturer waste stream prior to disposal. This definition is intended to include materials which are used to transport product to a consumer, including, for example, corrugated cardboard containers.

The term "region(s)" refer to portions or sections across the X-Y plane of the absorbent member.

The terms "ring roll" or "ring rolling" refer to a process using deformation members comprising counter rotating rolls, intermeshing belts or intermeshing plates containing continuous ridges and grooves where intermeshing ridges and grooves of deformation members engage and stretch a web interposed therebetween. For ring rolling, the deformation members can be arranged to stretch the web in the cross machine direction or the machine direction depending on the orientation of the teeth and grooves.

The term "rotary knife aperturing" (RKA) refers to a process and apparatus using intermeshing deformation members similar to that defined herein with respect to SELF or micro-SELF. The RKA process differs from SELF or micro-SELF in that the relatively flat, elongated teeth of a SELF or micro-SELF deformation member have been modified to be generally pointed at the distal end. Teeth can be sharpened to cut through as well as deform a web to produce an apertured web, or in some cases, a three-dimensionally apertured web, as disclosed in U.S. Patent Application Publication Nos. US 2005/0064136A1, US 2006/0087053A1, and US 2005/021753. RKA teeth can have other shapes and profiles and the RKA process can also be used to mechanically deform fibrous webs without aperturing the web. In other respects such as tooth height, tooth spacing, pitch, depth of engagement, and other processing parameters, RKA and the RKA apparatus can be the same as described herein with respect to SELF or micro-SELF.

The terms "SELF" or "SELF'ing", refer to Procter & Gamble technology in which SELF stands for Structural Elastic Like Film. While the process was originally developed for deforming polymer film to have beneficial structural characteristics, it has been found that the SELF'ing process can be used to produce beneficial structures in other materials, such as fibrous materials. Processes, apparatus, and patterns produced via SELF are illustrated and described in U.S. Pat. Nos. 5,518,801; 5,691,035; 5,723,087; 5,891,544; 5,916,663; 6,027,483; and, 7,527,615 B2.

The term "partially stratified", as used herein with respect to an absorbent member, means that some evidence of separation of portions of the absorbent member into layers is evident, but there remains some connection between parts of these layer so that they remain joined together (rather than delaminating and peeling off).

The term "unitary structure", as used herein, refers to a structure that either comprises: a single layer, or comprises fully-integrated multiple layers that are held together by hydrogen bonding and mechanical entanglement, and are not formed by assembling multiple layers that are formed separately and joined together with attachment means such as glue. An example of a unitary structure is a structure comprising different types of fibers (such as eucalyptus fibers that may be laid down over other cellulose fibers to form the outer layers for softness in tissue making).

The term "upper" refers to absorbent members, such as layers, that are nearer to the wearer of the absorbent article during use, i.e. towards the topsheet of an absorbent article; conversely, the term "lower" refers to absorbent members that are furthermore away from the wearer of the absorbent article towards the backsheet. The term "laterally" corresponds to direction of the shorter dimension of the article, which generally during use corresponds to a left-to-right orientation of the wearer. "Longitudinally" then refers to the direction perpendicular to the lateral one, but not corresponding to the thickness direction.

The term "Z-dimension" refers to the dimension orthogonal to the length and width of the member, core or article. The Z-dimension usually corresponds to the thickness of the member, core or article. As used herein, the term "X-Y dimension" refers to the plane orthogonal to the thickness of the member, core or article. The X-Y dimension usually corresponds to the length and width, respectively, of the member, core or article.

The term "zone(s)" refer to portions or sections through the Z-direction thickness of the absorbent member.

I. Absorbent Members

The present invention is directed to absorbent members and methods of making the same, and more particularly to bulked absorbent members and methods of making the same. In addition, if desired, the properties of the bulked absorbent members can be modified across the length and/or width of the absorbent member.

The absorbent members are made from a "precursor material" that is in the form of a web or sheet, comprising at least some cellulosic material, which may be a paper grade material. The precursor material may comprise any suitable wetlaid material, including but not limited to: drylap, liner board, paper board, post-consumer recycled material, filter paper, and combinations thereof. In some cases, the absorbent members may consist of, or consist essentially of, one of these wetlaid materials. The absorbent members described herein may, thus, be non-airlaid. As a result, the absorbent members may be substantially free, or completely free of binder material, such as latex binders sometimes used in making airlaid materials. The absorbent members described herein may, in some embodiments, also be substantially free, or completely free of absorbent gelling material, another common ingredient in airlaid materials.

The precursor material will typically comprise a plurality of individual fibers. A large proportion of cellulose fibers can provide for various advantages, such as keeping the cost of the web low. In particular aspects of the invention, the precursor material has a fiber content in which at least about 90 wt % of the fibers are cellulose, or fibers have a length of not more than about 0.4 inch (about 1 cm). Alternatively, at least about 95 wt %, and optionally, at least about 98 wt % of the fibers are cellulose, or fibers have a length of not more than about 0.4 inch (about 1 cm). In other desired arrangements, the precursor web can have a fiber content in which substantially about 100 wt % of the fibers are cellulose, or fibers have a length of not more than about 0.4 inch (about 1 cm).

The fibers comprising the precursor material include cellulosic fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred in certain embodiments since they may impart superior properties to the precursor material made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers. U.S. Pat. Nos. 3,994,771 and 4,300,981, describe layering of hardwood and softwood fibers. Also applicable to the present invention are fibers derived from recycled paper, which may contain any or all of the above categories as well as other non-fibrous materials such as fillers and adhesives used to facilitate the precursor web making. In addition to the above, fibers and/or filaments made from polymers, specifically hydroxyl polymers may be used in the present invention. Nonlimiting examples of suitable hydroxyl polymers include polyvinyl alcohol, starch, starch derivatives, chitosan, chitosan derivatives, cellulose derivatives, gums, arabinans, galactans and mixtures thereof.

The fibers comprising the precursor material will normally include fibers derived from wood pulp. Other natural fibers, such as cotton linters, bagasse, wool fibers, silk fibers, etc., can be utilized and are intended to be within the scope of this invention. Synthetic fibers, such as rayon, polyethylene and polypropylene fibers, may also be utilized in combination with natural cellulosic fibers. One exemplary polyethylene fiber which may be utilized is PULPEX®, available from Hercules, Inc. (Wilmington, Del.) Fibers formed from biopolymers made from non-petroleum sources such as bio-derived polyethylene (bio-PE), bio-derived polypropylene (bio-PP), bio-derived polyethylene terephthalate (bio-PET), and bio-derived poly(ethylene-2,5-furandicarboxylate) (bio-PEF) can also be used. These biopolymers can be partially or completely derived from at least one renewable resource where a renewable resource refers to a natural resource that can be replenished within a 100 year time frame. Renewable resources include plants, animals, fish, bacteria, fungi, and forestry products and may be naturally occurring, hybrids, or genetically engineered organisms. Natural resources such as crude oil, coal, and peat which take longer than 100 years to form are not considered to be renewable resources. Fibers having starch-based polymers and/or recycled resins such as post-consumer regrind r-HDPE, r-LLDPE, r-LDPE, r-PET, r-PEF, or r-PP can be also be used.

The fibers are typically held together by interfiber entanglement and hydrogen bonding. The fibers may have any suitable orientation. In certain precursor materials, the fibers will be aligned predominately in the direction of the process in which they were formed (or the "machine direction") of the forming process.

The precursor material may comprise additional layers of absorbent or non-absorbent materials to impart other properties, like strength. These could include, but are not limited to, scrims, films and nonwovens. Additionally, the precursor material may comprise superabsorbent particles or fibers.

FIG. 1 is a photomicrograph of one embodiment of a precursor material comprising dry lap. As shown in FIG. 1, the precursor material is a single layer structure that is generally relatively dense throughout its thickness. This precursor material is not suitable for use as a component of an absorbent article due to its lack of void volume and high stiffness. Table 1 in the Examples section shows the properties of one such precursor material. As shown in FIG. 1, there are some less dense portions at the surface of the precursor material, but these do not comprise a significant portion of the overall thickness of the precursor material. The methods described herein reduce the overall (that is, average) density and stiffness of the drylap (or other precursor material) and increase its void volume in at least some regions thereof so that it is suitable for use as an absorbent member in an absorbent article. The methods may also increase the average caliper of the precursor material.

The precursor material may have any suitable properties. In the case of a drylap precursor material, the burst strength of the precursor material may be as high as 1,500 kPa or more, measured according to TAPPI test method T 403 om-91 for Burst Strength. Generally, precursor materials with lower burst strengths are more easily mechanically modified to reduce their density (that is, "de-densified" by a "density reduction" process). Therefore, it may be desirable for the precursor material to have a burst strength less than 1,500, 1,400, 1,300, 1,200, 1,100, 1,000, 900, 800, 750, 700, 600, 500, 400, 300, 200, or 100 kPa, or less. The burst strength may also fall within any range between any of these burst strength numbers.

The precursor material may have any suitable caliper, basis weight, and density. Drylap generally has a caliper of at least about 0.04 inch or greater, e.g., from about 0.04 to about 0.06 inch (about 1-1.5 mm). However, applicants have had drylap specially made having calipers as low as 0.02 inch (about 0.5 mm). Thus, in some embodiments, the caliper of the precursor material may range from about 0.02 to about 0.06 inch (about 0.5-1.5 mm). Drylap that is commercially available typically has a basis weight of between about 100 and about 200 pounds/1,000 ft$^2$ (490-980 gsm). However, applicants have had drylap specially made having a basis weight as low as 20 pounds/1,000 ft$^2$ (98 gsm), or less. Thus, in some embodiments, the basis weight of the precursor material may range from about 20 pounds/1,000 ft$^2$ (98 gsm) to about 200 pounds/1,000 ft$^2$ (980 gsm). In some embodiments, the precursor web material may have a density of between about 0.25 g/cc and about 0.6 g/cc, or above, alternatively between about 0.3 g/cc and about 0.6 g/cc. Typically, such precursor materials will have a relatively uniform density throughout their thickness.

The precursor material may have any suitable moisture content. Drylap usually has a moisture content of less than about 10 percent, e.g., about 7 percent, although lower and higher moisture contents can be used. Generally, precursor materials with lower moisture contents are more easily mechanically modified to reduce their density ("de-densified"). For example, it may be desirable for the precursor web material to have a moisture content less than or equal to 10%, 9%, 8%, 7%, 6%, 5%, 4%, 3%, 2%, 1%, or any range between any of these percentages.

The precursor material may, in certain embodiments, be treated, partially treated (that is, having treated portions and untreated portions), or untreated. If the precursor material is treated, it may be provided with any suitable treatment, including but not limited to debonders such as chemical debonders. Examples of suitable treatments are described in U.S. Pat. Nos. 6,074,524, 6,296,737, 6,344,109 B1, and 6,533,898 B2. Typically, untreated precursor materials will have a higher burst strength than treated or partially treated precursor materials. Providing the precursor material with at least some treatment in the form of a debonder can permit the precursor material to be more easily mechanically modified to decrease its density.

Figure 2:
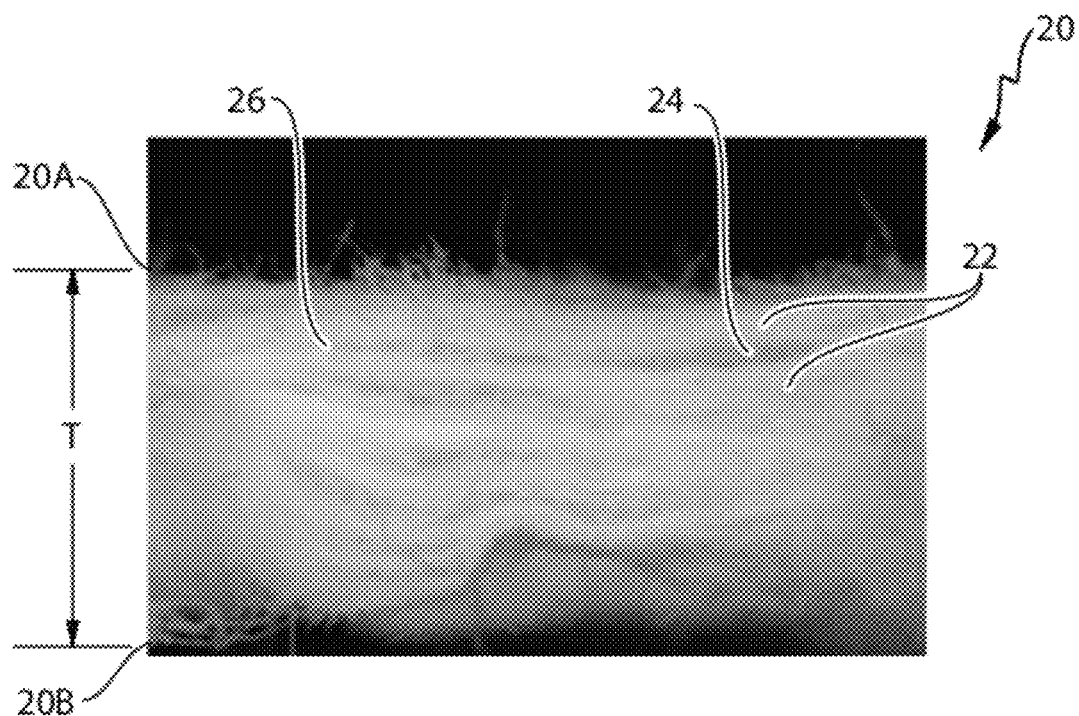
FIG. 2 is a photomicrograph of the cross-section of a web of dry lap after it has been processed according to one embodiment of the present method to form a bulked absorbent member.
Figure 3:
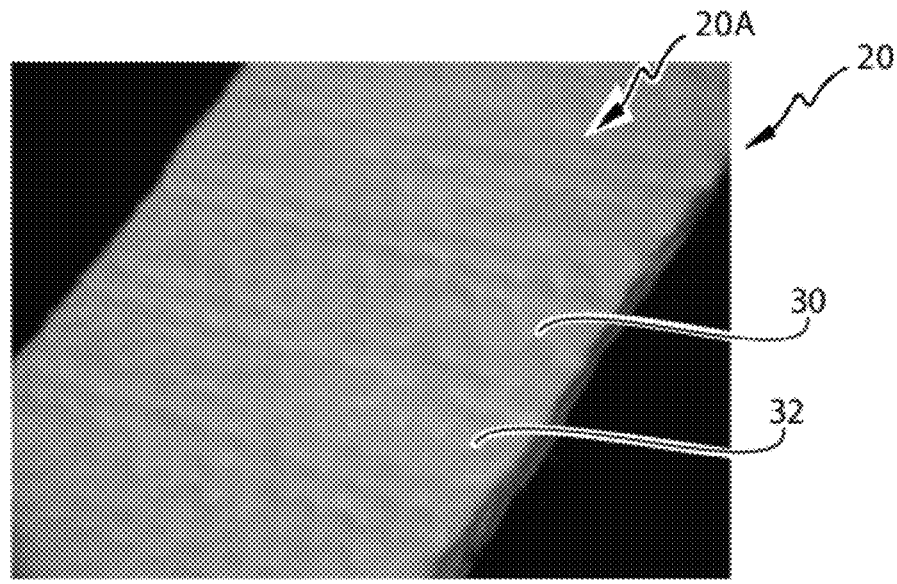
FIG. 3 is a top perspective view photograph of an absorbent member of the type shown in FIG. 2.
Figure 4:
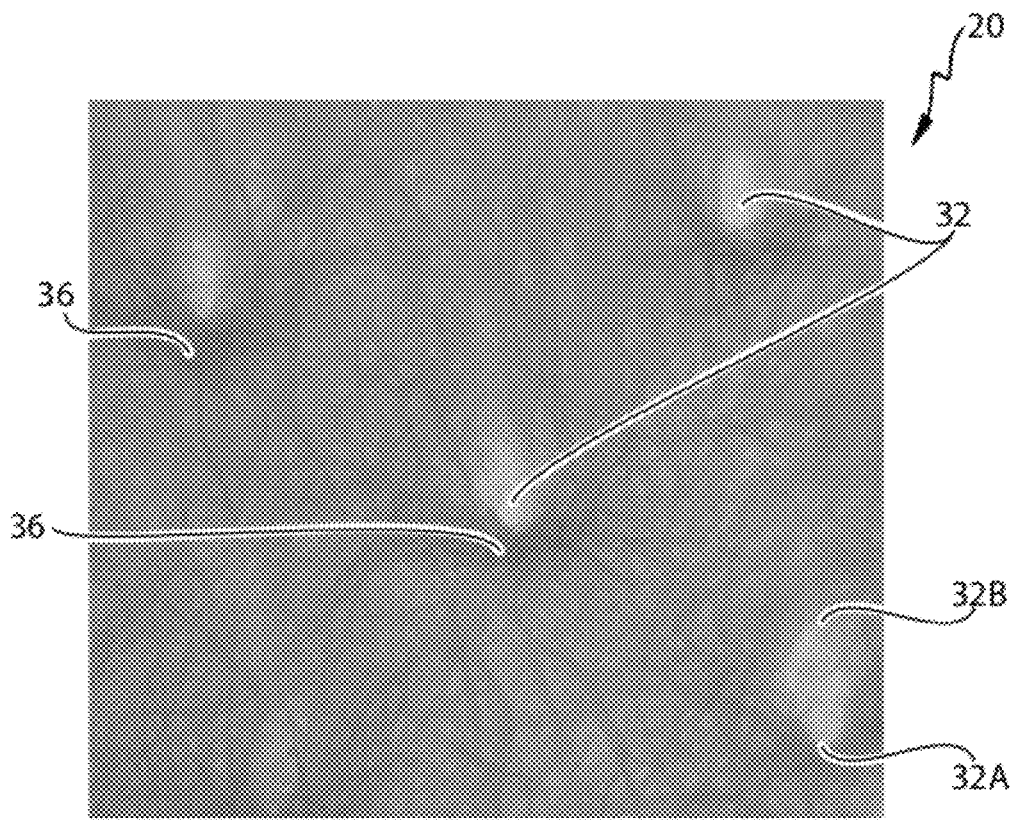
FIG. 4 is a magnified plan view photograph showing in greater detail, the surface of another variation of an absorbent member of the type shown in FIG. 2.

FIGS. 2-4 show one non-limiting example of a precursor web that was processed according to one embodiment of the present method to form a bulked absorbent member 20. The absorbent member 20 comprises a unitary absorbent fibrous structure having a first surface 20A, a second surface 20B, a length L extending in an X-direction, a width W extending in a Y-direction, and a Z-direction thickness T.

FIG. 2 shows that the absorbent member 20 is de-densified so that it is bulked or expanded. By "bulked" or "expanded", it is meant that the fibers have increased void spacing therebetween in comparison to the precursor material from which the absorbent member 20 is made (such as the precursor material shown in FIG. 1).

The precursor material may undergo a change in bulk density such that the absorbent member has a bulk density as low as 0.1, 0.2, 0.3, 0.4, 0.5, 0.6, 0.7, 0.8, or 0.9 times its original bulk density, or a change in bulk density in a range between any two of these numbers. Another way to describe the absorbent member 20 is that the absorbent member is comprised of cellulose fibers that have surfaces and there are interfiber hydrogen bonds between cellulose fibers that are substantially interrupted by void spaces between the fiber surfaces. Thus, at least a portion of the absorbent member 20 extending in the X-Y plane will have a thickness that appears to be "fluffed up" or lofted. The precursor material may also undergo a change in basis weight such that the absorbent member has a basis weight of 1.01-1.1 or higher times its original (precursor web) basis weight, especially when one of the rolls is set to run slower than the speed of the web during the process described below.

The absorbent members formed by the methods described herein may have any suitable overall properties. The absorbent member may have a bulk density range of between about 0.03-0.5 g/cc. It should be understood that the bulk density ranges of the various possible precursor materials and the absorbent members described herein may overlap. This is due to the wide variety of possible precursor materials. For a given precursor material, the bulk density of the absorbent member formed herein will be less than that of the precursor material. The methods described herein can form absorbent members with any suitable bulk density, including but not limited to a bulk density less than, equal to, or greater than 0.25 g/cc with high flexibility. The methods can also form absorbent members with any suitable thickness, including but not limited to less than or equal to 4 mm, or greater than 4 mm.

The absorbent member 20 may be partially de-layered or stratified. The differential speed between the penetrating teeth on opposing sides of the precursor web shears the web, selectively breaking fiber-to-fiber hydrogen bonds, forcing the material to partially separate into layers or strata 22, which increases the caliper and void volume of the absorbent member, and decreases the bulk density. As shown in FIG. 2, when it is said that the absorbent member is partially de-layered or stratified, it is meant that some evidence of separation of portions of the absorbent member into layers is evident creating spaces or zones 24 between layers, but there remains some connection between parts of these layers, such as at 26, so that they remain joined together (rather than delaminating and peeling off). Thus, in the case of a cellulosic precursor material, there may still remain some fibers connecting the strata. The strata 22 may have a higher density than the zones 24 between the strata, resulting in alternating zones of high and low density through the thickness of the material in the z-direction. These strata may have the same or a lower density than the precursor material.

The surface 20A of the absorbent member 20 may have a plurality of deformations or impact markings 30 therein. As shown in FIGS. 3 and 4, the deformations 30 may be in the form of depressions 32 extending at least partially into the thickness of the absorbent member, protrusions, or apertures 34 that pass completely through the thickness of the absorbent member. In some cases, the depressions 32, protrusions, or apertures 34 may be elongated in the machine direction and have a first end and a second end, such as first end 34A and second end 34B of apertures shown in FIG. 4.

Since, during the process, the teeth on the forming member that form the deformations or apertures are traveling at a different surface speed relative to the surface speed of the web, the teeth will essentially "plow" the material such that is it densified, and in many cased pushed up, at one end of the depression or aperture. These densified regions 36 may have a curvilinear plan view configuration that resembles the bow wave created by a boat traveling through water as shown in FIG. 4. This plowing effect may occur on one side or both sides of the web, depending upon the process used and the configuration of the forming members in the apparatus used to form the absorbent member.

Therefore, the opposite surface 20B likewise may have a similar pattern of deformations therein. However, in some embodiments, the densified regions 36 of the first surface 20A of the absorbent member are adjacent the first end portion of the depressions or apertures, and the densified regions on the second surface 20B of the absorbent member are adjacent the second end portion of the depressions or apertures. The bow waves on opposite surfaces in such an embodiment will point in opposite directions. The depressions or apertures created on one side of the web may be visible on the opposite side of the web and appear as protrusions or apertures, respectively. It should be understood that in the various different embodiments of the processes described herein, the deformations from the process may be more or less visible depending upon the process used and the configuration of the forming structure in the apparatus used to form the absorbent member. The deformations can be in any suitable form, including depressions, protrusions, apertures, or combinations thereof. The deformations can be arranged in any suitable pattern, including regular patterns or random patterns. The pattern of the deformations is a product of the process and apparatus used to reduce the bulk density of the precursor material.

II. Methods for Making the Absorbent Members

The methods of forming the absorbent members 20 involve subjecting the precursor web to at least one cycle or pass through a mechanical deformation process.

The mechanical deformation process can be carried out on any suitable apparatus that may comprise any suitable type(s) of forming members. Suitable types of forming apparatus include, but are not limited to: a pair of rolls that define a nip therebetween; pairs of plates; belts that define a nip therebetween; conveyor belts comprising pucks or plates that define a nip therebetween; or combinations thereof. Examples of belts and rolls that could be modified for use in the present methods are described in U.S. Pat. No. 8,021,591, Curro, et al. In the case of plates, at least one of the plates could move in the machine direction relative to the other plate as the plates come together to contact the precursor web in order to provide a similar motion to that of the rolls described herein. However, it is understood that the absorbent member produced by a pair of plates or belts could be different from that produced by rolls because of the reduced angles of engagement and disengagement present in a process comprising a pair of plates or belts. The absorbent member produced by plates or belts could be less bulked and the surface could be less disrupted. Although the apparatuses will be described herein for convenience primarily in terms of rolls, it should be understood that the description will be applicable to methods employing forming members that have any other configurations, in which case the other forming members may have forming elements (or teeth) of the configurations described below.

The rolls used in the apparatuses and methods described herein are typically generally cylindrical. The term "generally cylindrical", as used herein, encompasses rolls that are not only perfectly cylindrical, but also cylindrical rolls that may have elements on their surface. The term "generally cylindrical" also includes rolls that may have a step-down in diameter, such as on the surface of the roll near the ends of the roll, and rolls that are crowned. The rolls are also typically substantially non-deformable. The term "substantially non-deformable", as used herein, refers to rolls having surfaces (and any elements thereon) that typically do not deform or compress when used in carrying out the processes described herein. The rolls can be made from any suitable materials including, but not limited to steel or aluminum. The steel may be corrosion resistant and wear resistant steel, such as stainless steel.

Figure 5:
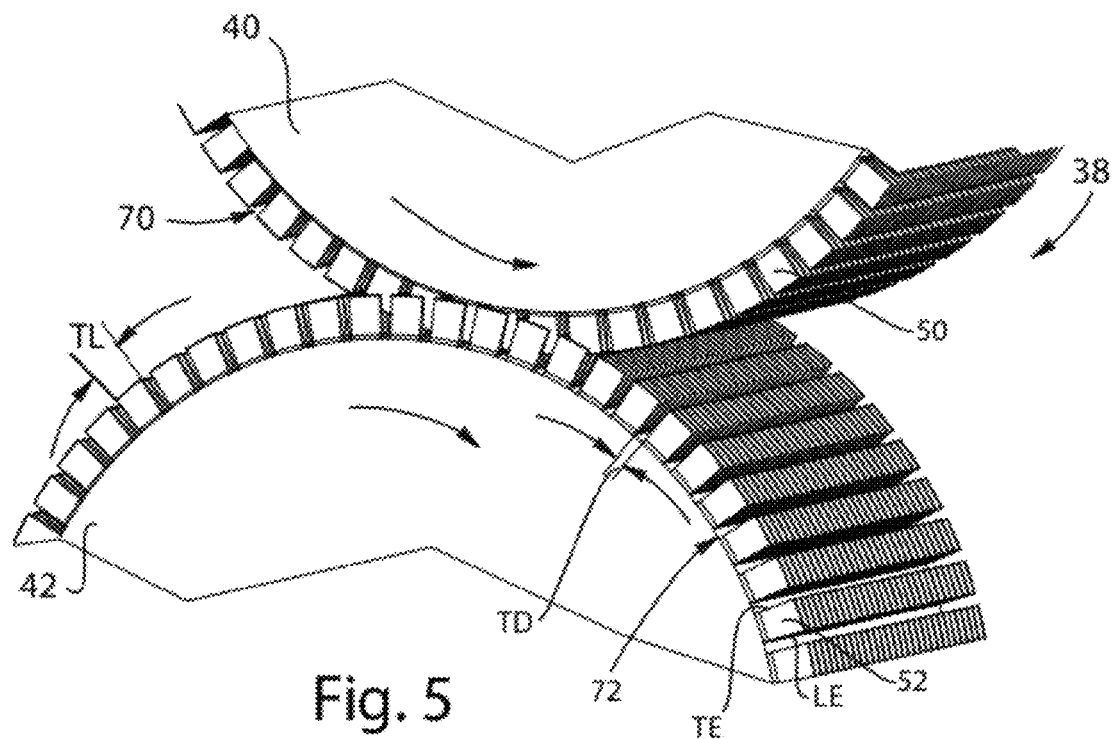
FIG. 5 is a perspective view of portions of two intermeshing rolls that may be used to form an absorbent member such as that shown in FIG. 2.
Figure 6:
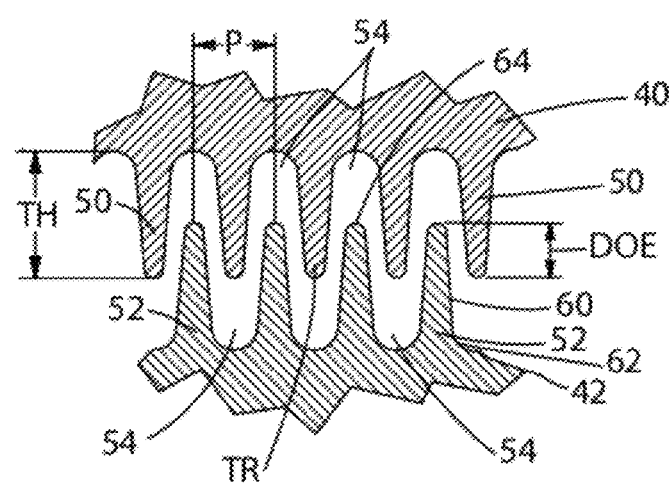
FIG. 6 is a cross-section of a portion of the intermeshing rolls.

The components of the forming apparatus 38, may, for instance, comprise a pair of rolls such as those shown in FIG. 5. The rolls 40 and 42 are each provided with forming elements comprising discrete protrusions or "male" elements 50 and 52 thereon that can intermesh with the surface of the opposing roll due to grooves 54 between male elements on each roll. The rolls are non-contacting, and axially-driven. The terms "intermeshing" or "meshing", as used herein, refer to arrangements when the forming elements on one of the components of the forming structure (e.g., roll) extend toward the surface of the other forming structure and the forming elements have portions that extend between and below an imaginary plane drawn though the tips of the forming elements on the surface of the other forming structure. As shown in FIGS. 5 and 6, the male elements on each roll may be arranged in rows so that they can be intermeshed and do not have to be phased in the machine direction (MD) as the rolls rotate. The top portions or tips of the forming elements on the different forming members are, thus, offset relative to each other in the nip, such that they do not align within a nip.

The rolls 40 and 42 in the pair of rolls will typically both rotate in opposite directions (that is, the rolls are counter-rotating) as shown by the arrows in FIG. 5. The rolls in at least one pair of rolls may rotate at different surface speeds. The same applies to various combinations of rolls and belts, or belts. (In the case of plates, however, the plates will typically move in the same direction (though they may move at different speeds). The rolls may rotate at different surface speeds by rotating the rolls at different axial speeds, by using rolls that have different diameters that rotate at the same axial speeds, or a combination of the two. The rolls may rotate at substantially the same speed as the speed at which the web is fed through the nip between the rolls; or, they may rotate at a greater or lesser speed than the speed at which the web is fed through the nip between the rolls. In cases where the rolls rotate at different speeds, there can be any suitable difference in surface or peripheral speeds between the rolls. The faster roll may have a surface speed that is anywhere from 1.02 up to about 3 times faster than the slower roll. Suitable ranges for the surface speed ratio include between about 1.05 and about 2.0, and more preferably between 1.05 and 1.4, depending on the geometry of the male elements. The greater the surface speed differential or ratio between the rolls, the greater the de-densification of the material.

The forming elements 50 and 52 on the rolls may have any suitable configuration. A given forming element can have the same plan view length and width dimensions (such as a forming element with a circular or square shaped plan view). Alternatively, the forming element may have a length, TL, that is greater than its width (such as a forming element with a rectangular plan view), in which case, the forming element may have any suitable aspect ratio of its length to its width. Suitable configurations for the forming elements include, but are not limited to: teeth having a triangular-shaped side view; elements having columnar shapes; elements having plan view configurations including circular, oval, hour-glass shaped, star shaped, polygonal, and the like, and combinations thereof. Polygonal shapes include, but are not limited to rectangular, triangular, pentagonal, hexagonal, or trapezoidal. The side-walls 60 of the forming elements 50 and 52 may taper at a constant angle from the base 62 to the tip 64, or they may change angles. The forming elements 50 and 52 can have tips 64 that are flat, rounded, or form a sharp point. Several examples of suitable configurations for the forming elements include, but are not limited to: SELF elements, RKA elements, shark fin, blunt shark fin, or pin shaped elements, and variations of the same. These are described in greater detail below with reference to FIGS. 7-11.

FIG. 5 is a close up of one non-limiting embodiment of the surfaces of two of the rolls 40 and 42 in a forming apparatus. The rolls 40 and 42 are carried on respective rotatable shafts (not shown) having their axes of rotation disposed in a parallel relationship. In this embodiment, each of the rolls 40 and 42 comprises one of The Procter & Gamble Company's SELF technology rolls.

The forming elements 50 and 52 on the SELF rolls can be oriented in either the machine direction (MD) or the cross-machine direction (CD). As shown in FIG. 5, the SELF rolls may comprise a plurality of alternating circumferential ridges and grooves around the circumference of the roll. The ridges have spaced apart channels 70 and 72 (on rolls 40 and 42 respectively) formed therein that are oriented parallel to the axis of the rolls. The channels 70 and 72 form breaks in the ridges that create forming elements or teeth 50 and 52 on the SELF rolls. In such embodiments, the teeth 50 and 52 have their longer dimension oriented in the machine direction (MD). These roll configurations will be referred to herein as a "CD SELF" roll, since in the usual SELF process, the material being fed into a nip formed by such a roll would be stretched in the cross-machine direction (or "CD").

Figure 29:
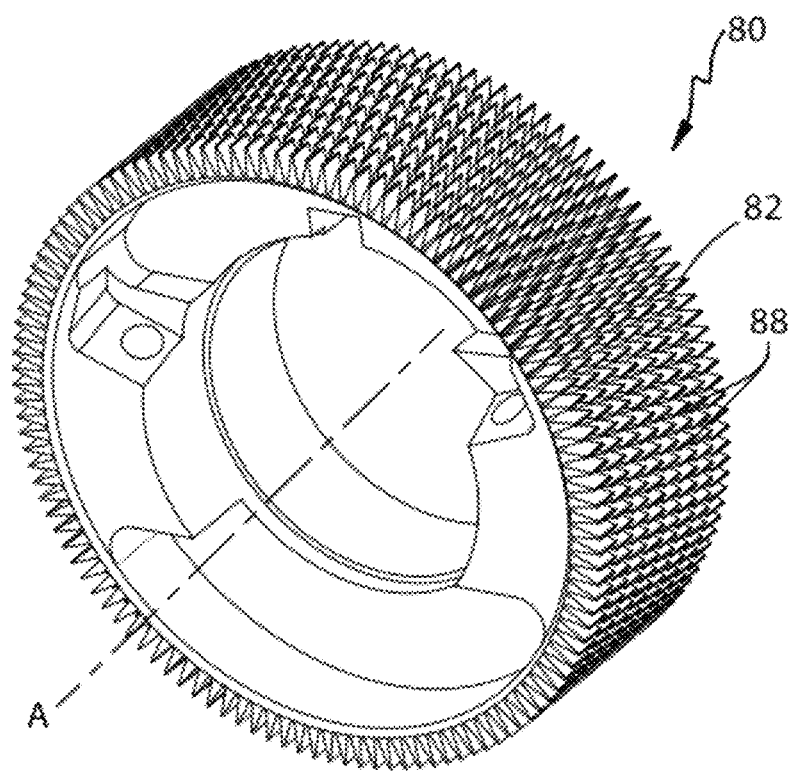
FIG. 29 is a perspective view of another example of another forming member for an optional step of forming the precursor web into a three dimensional absorbent member.

In other embodiments (such as shown in FIG. 29), the SELF roll 80 can comprise a machine direction, or "MD SELF" roll. Such a roll will have alternating ridges and grooves that have their longer dimension oriented parallel to the axis A of the roll (that is, in the cross-machine direction (CD)). The ridges in such a roll 80 have spaced apart channels 88 formed therein that are oriented around the circumference of the roll. The channels form breaks in the ridges to form forming elements or teeth on the MD SELF roll.

Figure 20:
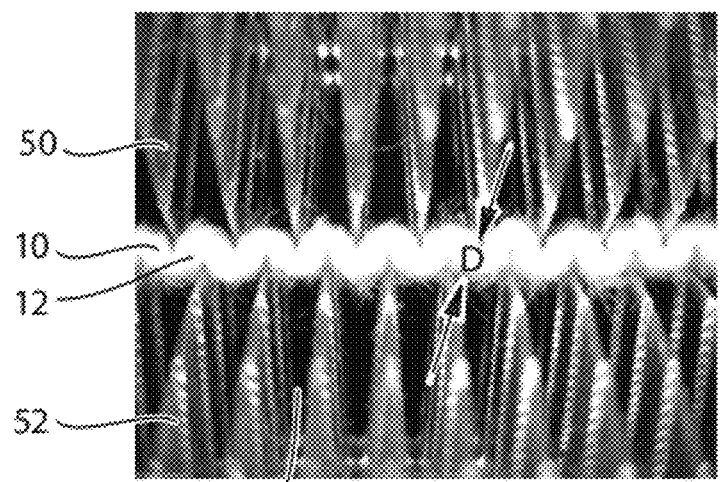
FIG. 20 is a photograph of a web in a nip between intermeshing rolls.

The process used herein differs from Procter & Gamble's SELF process in a number of respects. One distinction is that the web materials described herein will typically not be formed into structures provided with rib-like elements and elastic-like properties. Rather, as shown in FIG. 20, the SELF process is used in the present context to mechanically deform the precursor web material 10 and induce shear forces in localized areas 12 between the teeth 50 and 52 of the forming members by running them at different surface speeds (or, in some cases, at the same surface speeds in the optional steps described below) in order to selectively break hydrogen bonds of the web 10, to reduce the bulk density and increase the flexibility of the precursor web material.

As shown in FIG. 6, the teeth 50 and 52 of one roll extend partially into the grooves 54 of the opposed roll to define a "depth of engagement" (DOE), which is a measure of the level of intermeshing of rolls 40 and 42. The depth of engagement can be zero, positive for meshing rolls, or negative for non-meshing rolls. In the case of the rolls shown in FIG. 5, the male elements are intermeshed at a relatively high DOE. The DOE can include but not be limited to values greater than the thickness of the precursor web.

FIG. 6 shows in cross section a portion of the intermeshing rolls 40 and 42 including teeth 50 and 52 and grooves 54 between the teeth 50 and 52. The teeth 50 and 52 in this embodiment have a triangular or inverted V-shape when viewed in cross-section. The vertices or tips 64 of teeth are outermost with respect to the surface of the rolls. As shown, the teeth 50 and 52 have a tooth height TH, a tip radius TR, a tooth length TL (FIG. 5), an MD tooth-to-tooth spacing TD and a CD tooth-to-tooth spacing (or ridge-to-ridge spacing) referred to as the pitch P. The tooth length TL in such embodiments is a circumferential measurement. The outermost tips of the teeth have sides that are preferably rounded to avoid cuts or tears in the precursor material. The leading and trailing edges LE and TE (FIG. 5), respectively, of the teeth 50 and 52 may, in some cases, be square or a shape that creates a relatively sharp edge to maximize de-densification of the web in the process.

For making an absorbent member 20 such as that shown in FIGS. 2-4 from a precursor web having a basis weight in the range of from about 200 to 700 gsm, the teeth 50 and 52 may have a length TL ranging from about 0.5 mm (0.020 inch), or less, to about 10 mm (0.400 inch), alternatively from about 2 mm (0.080 inch) to about 6 mm (0.240 inch), and a MD spacing TD from about 0.5 mm (0.020 inch) to about 20 mm (0.800 inch), alternatively from about 1 mm (0.040 inch) to about 4 mm (0.160 inch), a tooth height TH ranging from about 0.5 mm (0.020 inch) to about 10 mm (0.400 inch), alternatively from about 2 mm (0.080 inch) to about 5 mm (0.200 inch), a tooth tip radius TR ranging from about 0.05 mm (0.002 inch) to about 2.0 mm (0.080 inch), alternatively from about 0.1 mm (0.004 inch) to about 0.5 mm (0.020 inch), and a pitch P between about 1 mm (0.040 inches) and 10 mm (0.400 inches), alternatively from about 2 mm (0.080 inch) to about 4 mm (0.160 inch). The depth of engagement DOE can be from about 1 mm (0.040 inch) to about 5 mm (0.200 inch) (up to a maximum approaching the tooth height TH). Of course, DOE, P, TH, TD, TL, and TR can each be varied independently of each other depending on the properties of precursor web 10 and the desired characteristics of the absorbent member 20. In addition, the shape and geometry of the teeth on the first roll can be the same or different from the shape and geometry of the teeth on the second mating roll.

Figure 7:
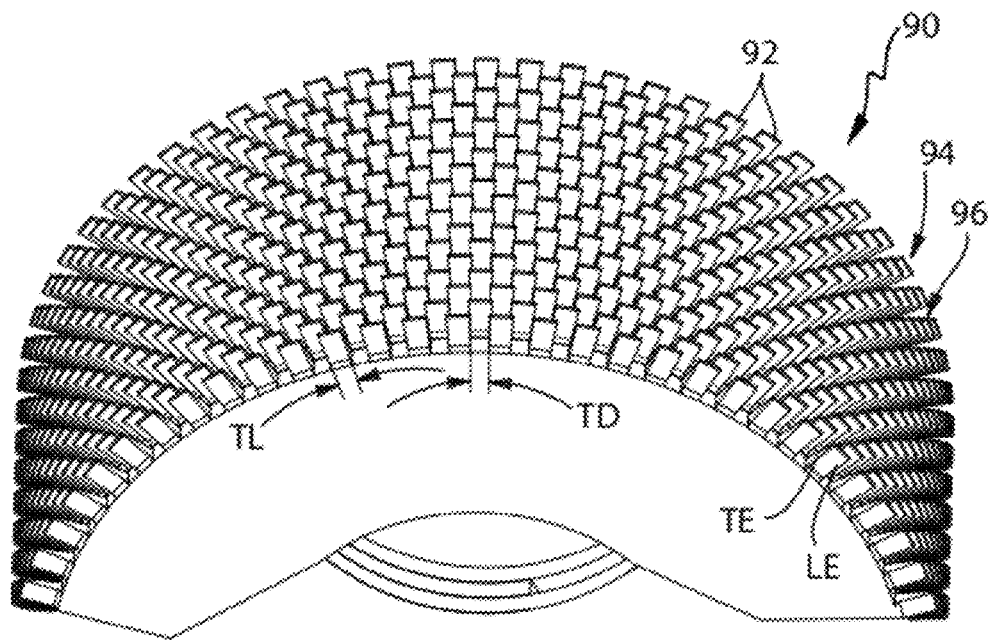
FIG. 7 is a perspective view of another embodiment of a roll that can be used in the methods described herein.

FIG. 7 shows an embodiment of a roll 90 that will be referred to herein as a "staggered CD SELF" roll. As shown in FIG. 7, the surface of the roll 90 has a plurality of spaced apart teeth 92. The teeth 92 are arranged in a staggered pattern. More specifically, the teeth 92 are arranged in a plurality of circumferentially-extending, axially-spaced rows, such as 94 and 96, around the roll. Again, but for the spacing TD between the teeth in each row, the teeth in each roll would form a plurality of circumferentially-extending, axially-spaced alternating ridges and grooved regions. However, in this case, the teeth 92 in adjacent rows are offset, or staggered, relative to each other. The tooth length TL and machine direction (MD) spacing TD can be defined such that the teeth in adjacent rows 94 and 96 either overlap or do not appear to overlap when the rolls are viewed from one of their ends. In the embodiment shown, the teeth 92 in adjacent rows are circumferentially offset by a distance of 0.5× (where "x" is equal to the tooth length plus the MD spacing TD between teeth in a given row). In other words, the leading edges LE of adjacent teeth in adjacent rows will be offset in the MD by 0.5×. Such a roll 90 may be aligned with another roll to form a nip so that the rows of teeth in one roll align with the grooved regions between the teeth in the other roll. The roll shown in FIG. 7 can be made in any suitable manner, such as by first cutting the ridges and grooves into the roll, then helically cutting the teeth 92 into the surface of the roll with each cut being continuous. If desired, the tooth profile (in particular, the leading and trailing edges) can be modified by using a plunge cut.

Figure 8:
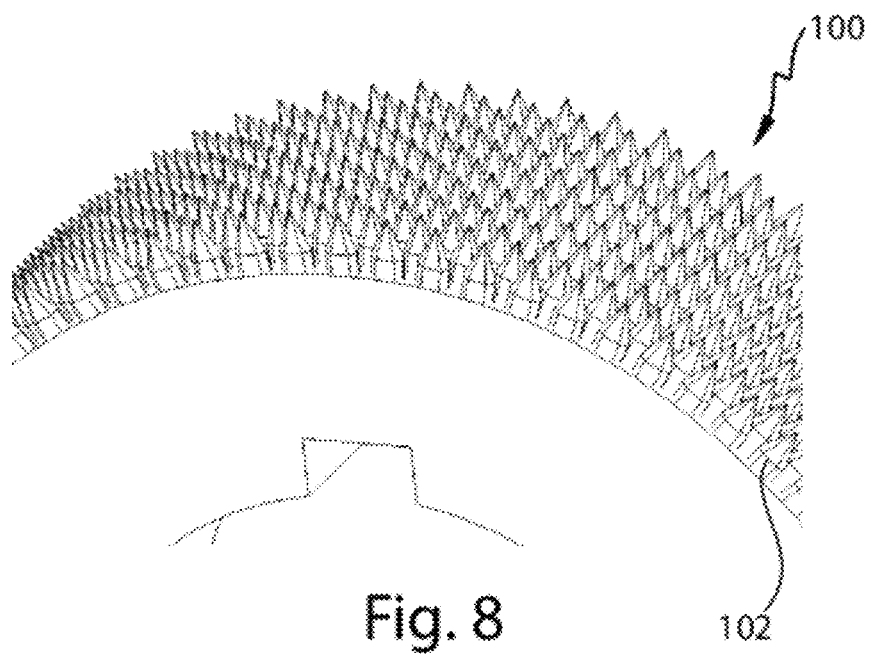
FIG. 8 is a perspective view of one embodiment of a roll that can be used in the methods described herein.

FIG. 8 shows a portion of the surface of a roll 100 having male elements 102 of another configuration that can be used in the method. The roll shown in FIG. 8 is referred to herein as a Rotary Knife Aperturing (or "RKA") roll. As shown in FIG. 8, the roll 100 comprises circumferentially-extending alternating rows of teeth 102 and grooves therebetween. The teeth 102 have a pyramidal tooth shape and can have up to six sides, each side being generally triangular in shape. The teeth 102 are joined to the bottom roll at their bases. The bases of the teeth have a cross-sectional length dimension greater than a cross-sectional width dimension. The teeth 102 can taper at a constant angle from their base to their tip, or the angle of taper can change, as in the tooth shown in FIG. 8. FIG. 8 shows an example of teeth having sides that are truncated at the base such that a portion of the sides of the teeth adjacent the base are substantially vertical before the teeth begin to taper toward their tips. RKA rolls are described in greater detail in U.S. Patent Application Publication No. US 2006/0087053 A1.

Figure 9:
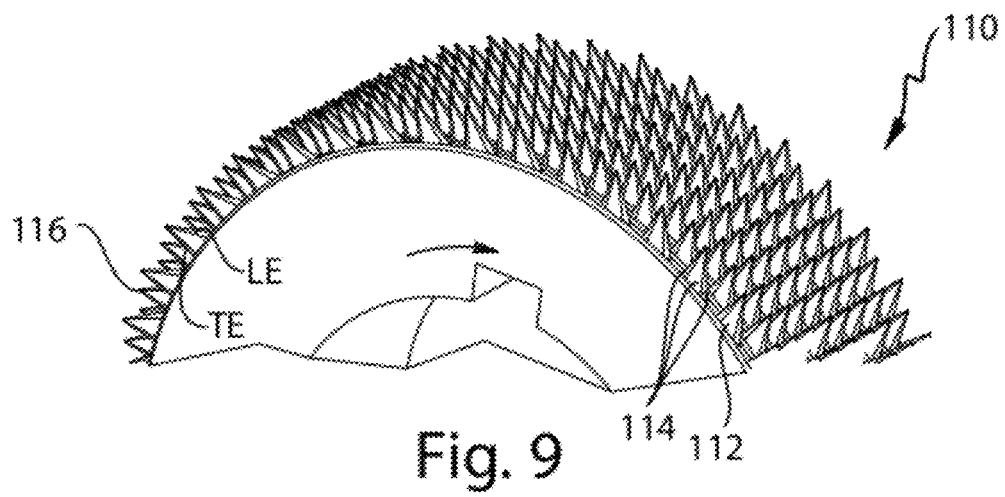
FIG. 9 a perspective view of another embodiment of a roll that can be used in the methods described herein.

FIG. 9 shows a portion of the surface of a roll 110 having male elements 112 of another configuration that can be used in the method. In this embodiment, the leading edge LE and trailing edge TE form different angles with the surface of the roll, and resemble the shape of a shark's fin (which may be referred to as a "shark fin tooth"). The leading edge LE may form a greater angle with the surface of the roll than the trailing edge TE. In some cases, the trailing edge TE may form an angle that is generally perpendicular to the surface of the roll. In the version of the shark fin tooth shown in FIG. 9, the shark fin tooth 112 has a generally pointed pyramidal shape with six sides 114 (three of which are shown on the half of the tooth depicted), where each side is generally triangular in shape. The vertex of two sides makes up the leading edge LE and the vertex of two sides makes up the trailing edge TE of tooth 112. The vertices of the leading or trailing edge can be relatively sharp, or in other cases, they can be machined to have a rounded radius of curvature. As shown in FIG. 9, the teeth can taper at a constant angle from their base to their tip, or the angle can change. The teeth can also have less than six sides, for example, if the LE and TE are squared off instead of forming a vertex.

Figure 10:
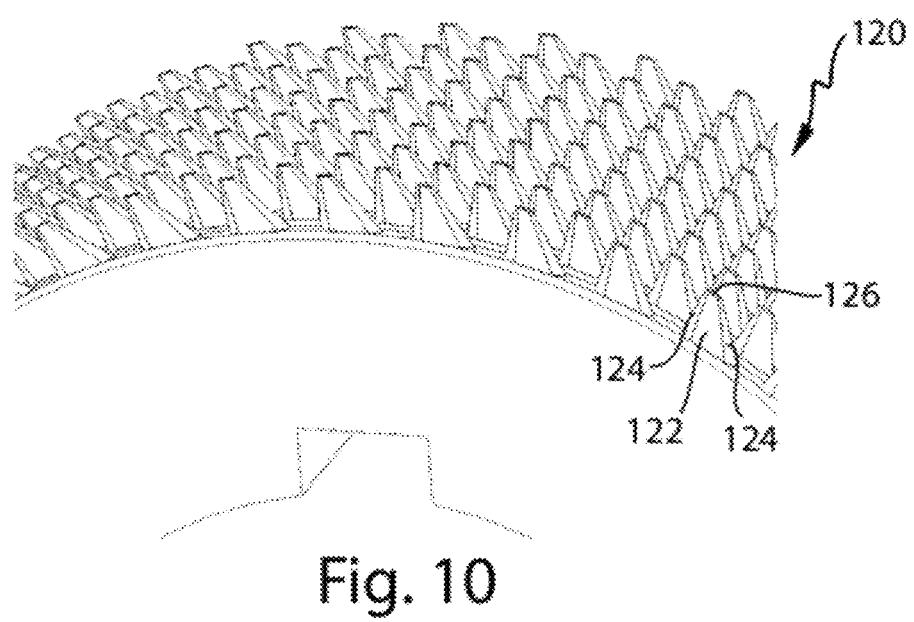
FIG. 10 is a perspective view of another embodiment of a roll that can be used in the methods described herein.

FIG. 10 shows a portion of the surface of a roll 120 having male elements 122 of another configuration that can be used in the method. The roll shown in FIG. 10 is referred to herein as a "blunted shark fin" roll. As shown in FIG. 10, the generally pyramidal shapes shown in FIG. 9 can be truncated so as to remove the pointed tips 116 and create a frustum. Truncation can be made at a predetermined distance from the base of the tooth such that a generally flattened region 126 is produced at the distal end of tooth 122. The generally flattened region 126 can have an area shape corresponding to the cross-sectional shape of tooth 122. Thus, generally flattened region 126 can also be elongated, that is, having a length dimension greater than a width dimension and an aspect ratio AR corresponding to the aspect ratio of tooth 122. In one embodiment, the flattened region 126 can transition to sides 124 at generally sharp vertices. In other embodiments, the transition can be at a radius of curvature, providing for a smooth, rounded, flattened tooth tip. Any other tooth shapes described herein can be truncated as well to form different frustum tooth shapes.

Figure 11:
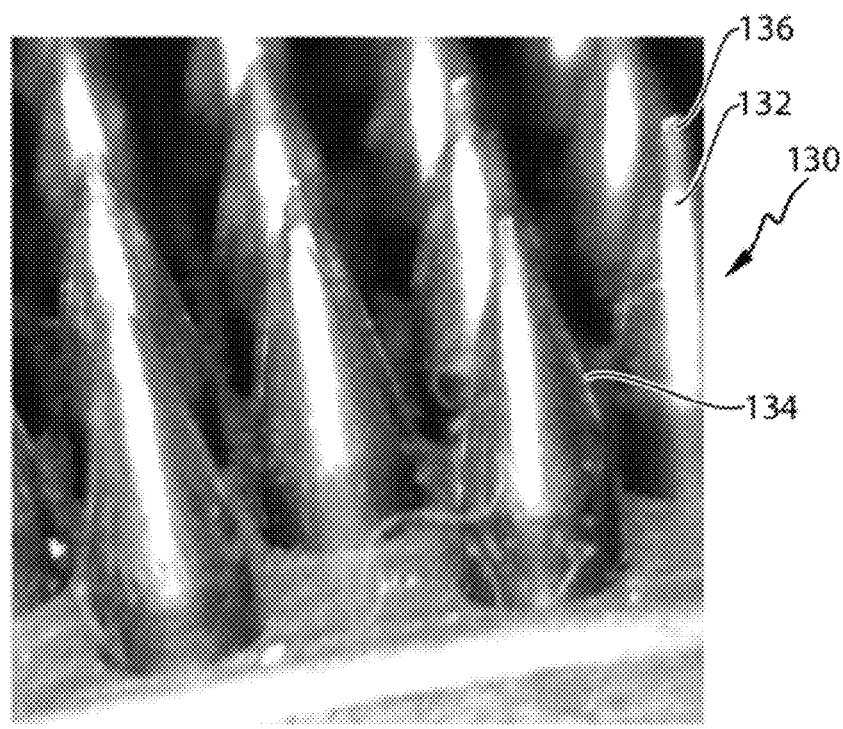
FIG. 11 is a perspective view photograph of the surface of another embodiment of a roll that can be used in the methods described herein.

FIG. 11 shows a portion of the surface of a roll 130 having male elements 132 of another configuration that can be used in the method. The roll shown in FIG. 11 is referred to herein as a "pin" roll. Unlike some of the previous tooth geometries described, the teeth 132 of a pin roll are not faceted, meaning they do not comprise flat faces. The pin tooth 132 can have various cross-sectional shapes, such as round or oval. The tip 136 of the tooth can come to a sharp point, be rounded, or be truncated so it has a flat surface. The tooth can also be bent at an angle. The side wall 134 can taper from the base to tip at a constant angle, or the side wall can change angles. For example, the top of the tooth 130 can have a cone-like shape with a 30 degree angle between the axis of the tooth and the side wall 134, and the base of the tooth can have a cylindrical shape with a vertical side wall that runs parallel to the axis of the tooth.

The rolls having the various configurations described herein can be mated together in any suitable combinations to form a nip therebetween. A roll can be intermeshed with another roll comprising the same or different pattern, but must be done in a way such that the teeth do not come in contact with each other. The two mating rolls can be aligned such that the rows of teeth on the first roll are offset (or placed in between) in the CD from the rows of teeth on the second roll.

For some combinations of rolls, various processing aides are necessary to remove the web from one or both of the rolls after the web passes through the nip. For example, non-stick treatments, such as silicone or fluorocarbon treatments can be added. Other methods of aiding the removal of the web from the rolls include air knives or brushing. In one embodiment, at least one of the rolls can have an internal chamber and means to provide positive air pressure at the point of web removal. In still other embodiments, the apparatus can be provided with a web removal system in the form of a comb or wrapped wires that can penetrate into the grooves of the roll and actively lift the web out of the grooves.

Figure 12:
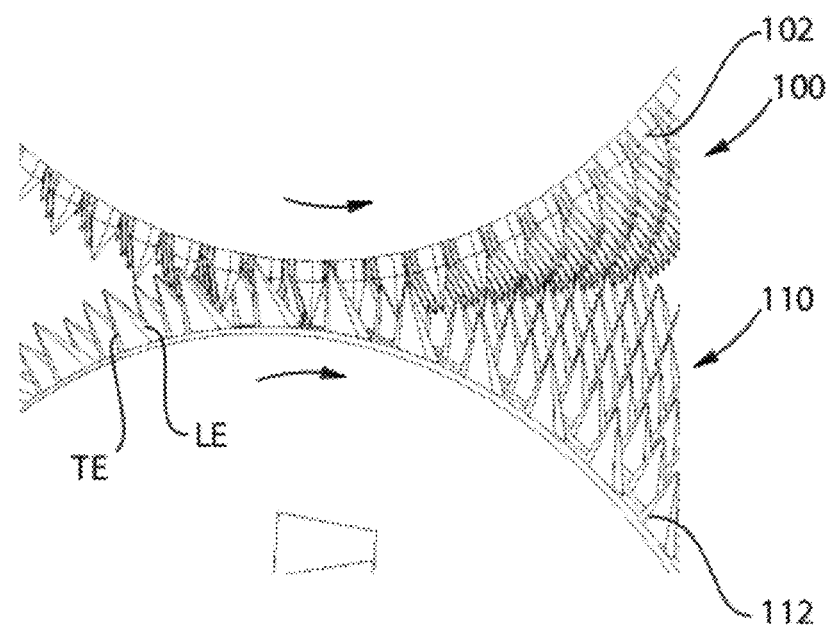
FIG. 12 is a perspective view of portions of two intermeshing rolls that may be used to form an absorbent member.
Figure 13:
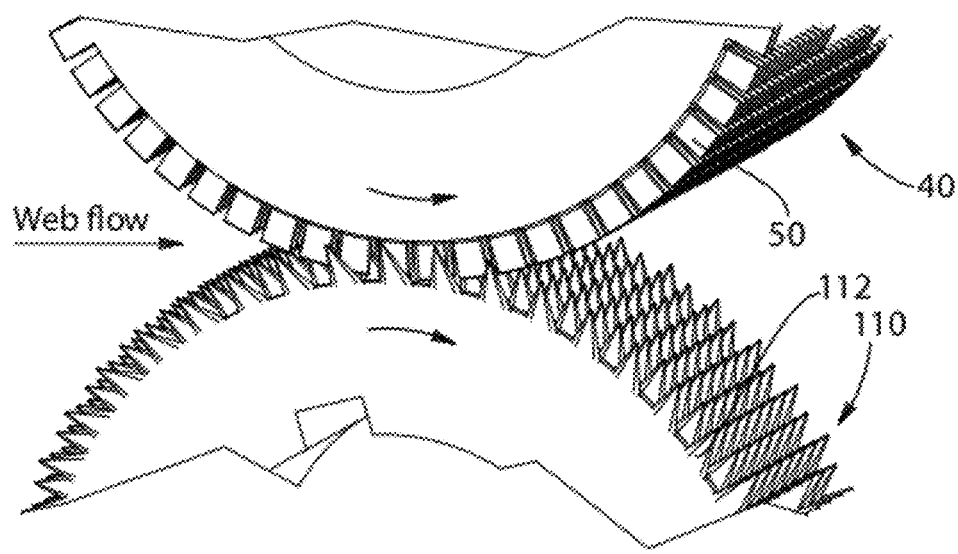
FIG. 13 is a perspective view of portions of an alternative embodiment of two intermeshing rolls that may be used to form an absorbent member.

FIGS. 12 and 13 show two non-limiting variations of suitable roll combinations. FIG. 12 shows a mating roll combination formed by an RKA roll 100 (shown on top) and a shark fin roll 110 on bottom. Of course, in other embodiments, the positions of the two rolls could be reversed. The shark fin roll 110 has been found to help reduce the force to remove the web from the roll and eliminate the need for a web removal aide on that roll. It is believed that the same would be the case for any tooth shape with a leading edge LE that is angled to be greater than 90 degrees from the surface of the roll. The angle referred to is measured between the portion of the surface of the roll outside the tooth to the leading edge. Typically, one roll speed will be close to that of the web, and the mating roll speed will be slower than that of the web. For a shark fin roll mated to an RKA roll (or other type of roll), the shark fin roll will typically be the faster rotating roll. The surface speed ratio of the faster roll relative to the slower roll can be any suitable amount greater than or equal to 1.02, 1.05, 1.1, 1.5, 2.0, or 3.0.

FIG. 13 shows a mating roll combination formed by a CD SELF roll 40 (shown on top) and a shark fin roll 110 on bottom. In other embodiments, the positions of the two rolls could be reversed. Various suitable roll combinations include, but are not limited to the following mating roll configurations: SELF/SELF, RKA/shark fin (FIG. 12), SELF/shark fin (FIG. 13), shark fin/shark fin, SELF/pin, pin/shark fin, and pin/pin.

Figures 14, 14A:
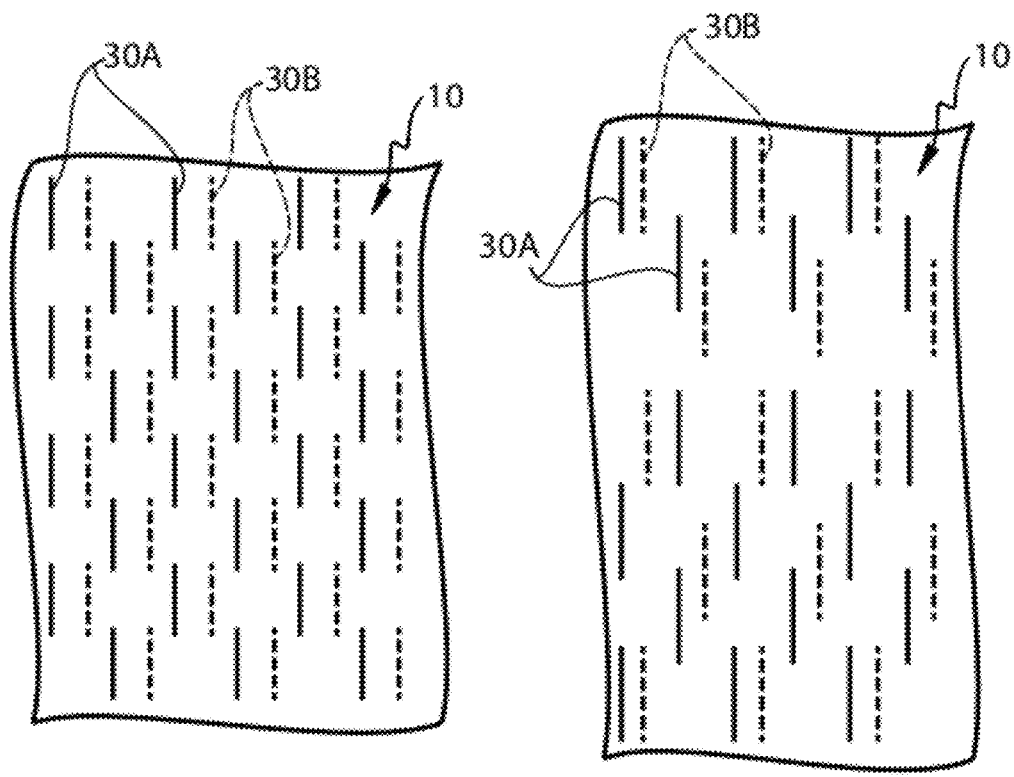
FIG. 14 is a schematic plan view of an area on a web showing how the teeth on the two rolls could align in the nip.
FIG. 14A is a schematic plan view of an area on a web showing an alternative arrangement for how the teeth on the two rolls could align in the nip.

The process can, if desired, be designed such that the teeth in the nip on the first roll can be phased with the teeth in the nip on the second roll. As a result, the teeth in the nip on the first roll may always have the same relative position to the teeth in the nip on the second mating roll, resulting in a consistent, repeating pattern of deformations on the web (even though the rolls are rotating at different speeds). FIG. 14 is a schematic plan view of an area on a web 10 showing an example of how the teeth on the two mating rolls (in this case two staggered CD SELF rolls such as shown in FIG. 7) could align in the nip to create a consistent, repeating pattern on the web. FIG. 14 shows the areas 30A impacted on a web by teeth on a first roll and areas 30B impacted by the teeth on a second roll. Each of the deformations from the first roll are always at the same relative position to the adjacent deformations made by the second roll. The term "adjacent", as used in this context, refers to the closest deformation made by the other roll, even though the deformation may be on the opposite surface of the web. The process can be designed multiple ways to achieve this, including the following.

In one embodiment, the two mating roll diameters can be the same, and the rolls can be run at different axial speeds or revolutions per minute (rpms), and the MD tooth repeat length on at least one roll can be varied such that the ratio of the rpm of the first roll to the second roll is equal to the ratio of the MD tooth repeat length of the first roll to the second roll. The term "MD tooth repeat length" as used herein refers to the sum of the tooth length TL and the MD tooth-to-tooth spacing TD between the teeth.

In another embodiment, the rolls can be run at the same axial speed or rpm, and the roll diameter and MD tooth repeat length can be varied such that the ratio of the diameter of the first roll to the second roll is equal to the ratio of the MD tooth repeat length of the first roll to the second roll.

Alternatively, the process can be designed such that the teeth in the nip on the first roll are not phased to the teeth in the nip on the second mating roll and, therefore, the teeth on the first roll will not maintain a consistent MD position from one row of teeth to the next relative to the teeth on the second roll. FIG. 14A is a schematic plan view of an area on a web 10 showing an example of how the teeth on the two mating rolls (two staggered CD SELF rolls) could create a varying pattern, but still repeating at some interval. FIG. 14A shows the areas 30A impacted on a web by teeth on the first roll and areas 30B impacted by the teeth on the second roll. What is meant by "varying" is that the deformations from the first roll are not always in the same relative position to the adjacent deformations from the second roll from one row of teeth to the next. However, the pattern does repeat. In the example shown in FIG. 14A, the pattern repeats every seventh row of teeth on the first roll and every fifth row of teeth on the second roll. The repeat length will depend on the surface speed ratio, diameter and MD tooth repeat length of the two mating rolls.

The precursor web can be fed through the mechanical deformation process in any suitable orientation if the precursor web is in the form of sheets. If the precursor material is in the form of sheets, the individual sheets can be joined with their ends in an overlapping configuration by passing the sheets through a nip of an RKA or SELFing process. Typically, the precursor material will be fed into the mechanical deformation process in the machine direction if it is in roll form.

III. Other Alternative Embodiments

There are numerous other alternative embodiments of the methods described herein that can be used to provide the absorbent members with various different properties.

All of the methods may involve a density reduction (or "de-densification") step. The density reduction step can utilize a single nip apparatus that is formed by forming members moving at different surface speeds as described above (that is, a "differential speed" nip).

In some alternative embodiments, the forming members forming the differential speed nip may be configured with forming elements in arrangements that are varied over the surfaces of the forming members in order to provide the absorbent member with regional property variations.

In some alternative embodiments, the density reduction step can utilize more than one nip (that is multiple nips). In these latter embodiments, the multiple nips may each be formed by differential speed nips. Alternatively, the apparatus may comprise a "hybrid" process in which the multiple nips comprise at least one differential speed nip, and at least one nip is formed by forming members that are moving at substantially the same surface speed ("matched speed" nips). In many embodiments, it may be desirable for there to be multiple matched speed nips. The forming members that form the matched speed nips may be arranged in a number of different configurations including, but not limited to "nested" configurations as described below. The differential speed nip(s) and the matched speed nips may be arranged in any order (in a process). The matched speed nip(s) may, in some cases, be configured to provide the precursor material with reduced density zones on each side of the precursor material (a "two side de-densified" precursor material), or a reduced density zone on one side of the precursor material (a "one side de-densified" precursor material).

In any of the foregoing methods, the precursor web 10 may be further subjected to a pre-processing step (that occurs before the density reduction step) and/or a post-processing step (that occurs after the density reduction step). The pre-processing step and post-processing step may utilize at least one matched speed nip that provides the absorbent member with various additional properties.

A. Methods of Providing Absorbent Members with Regional Property Variations.

Figure 15:
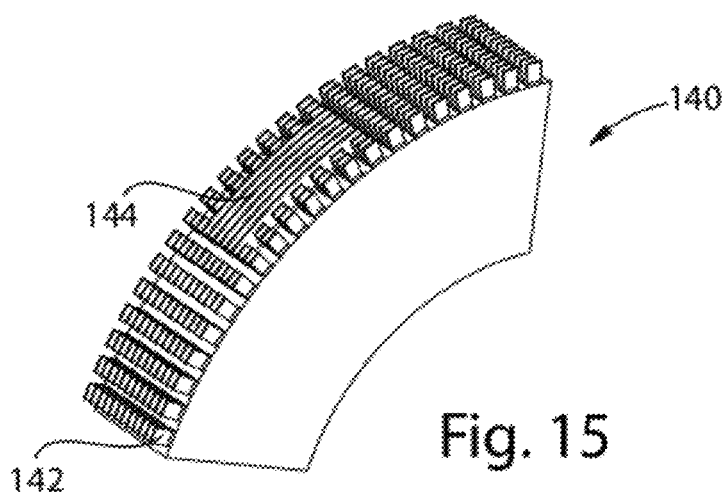
FIG. 15 shows a perspective view of the surface of another embodiment of a roll that can be used in the methods described herein.

FIG. 15 shows an embodiment in which the surface of at least one of the rolls 140 can be zoned so that different material properties will be created in different regions of the material or product. Although many variations are possible, the surface of the roll 140 shown comprises a first region comprising CD SELF teeth 142, having a first height, and a second region comprising ring rolling ridges and grooves 144, in which the ridges have a second lower height than the SELF teeth 142. For example, the web processed by the roll in FIG. 15 may have regions that are more de-densified (by the SELF teeth), and have greater thickness and flexibility, than other regions in the web (impacted by the lower height ring roll ridges). The surfaces of the forming members (that is, the tooling) may have differences in regions that could include differences in: tooth shape, tooth height, tooth length, tooth spacing, continuous ridges in place of discrete teeth, the absence of teeth on one or both forming members, etc. A roll having regions with forming elements of different properties across its surface may be used in the differential speed nip; or, in a matched speed nip for pre- or post-processing the precursor web.

In other embodiments, the absence of teeth on one or both forming members over a portion of the surface of the forming member(s) can be used to provide the absorbent member with regional de-densification. The term "regional de-densification" refers to an absorbent member which has some portions that are not de-densified. In order to make an absorbent member with regional de-densification, the precursor web is de-densified only in select areas/regions in the X-Y plane. This can be done by providing selected portions of the forming members which are free of forming elements such that they will leave portion(s) of the precursor web material in their original state.

B. Methods Employing Multiple Nips.

1. Methods Utilizing Multiple Differential Speed Nips.

Figure 16:
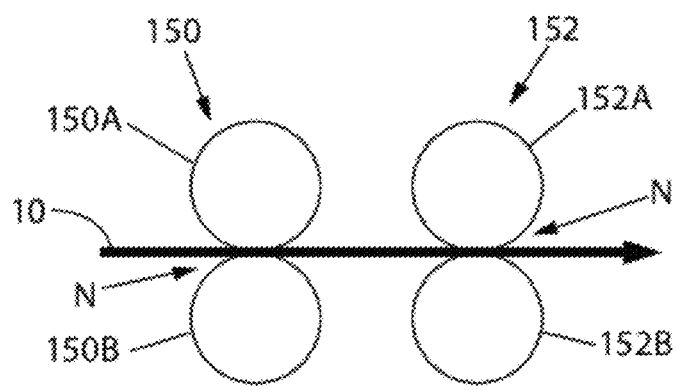
FIG. 16 is a schematic side view of one embodiment of an apparatus for making an absorbent member.

FIG. 16 shows an apparatus that comprises two pairs of rolls 150 and 152 and may be referred to as a "paired roll" apparatus. Each pair of rolls comprises two rolls, 150A and 150B, and 152A and 152B, respectively, that forms a single nip N therebetween. In the embodiment shown in FIG. 16, four rolls are shown. However, the apparatus can comprise any suitable number of rolls. Multiple rolls are useful when it is desirable to run the precursor web 10 through multiple nips.

Multiple nips formed by differential speed rolls may be used to further enhance the properties of the precursor web, such as: increasing caliper/bulk; decreasing surface density for faster fluid acquisition; and/or increasing flexibility. In any embodiments in which there are two or more pairs of rolls, one or more of the following properties of the pairs of rolls can be varied relative to another pair of rolls: forming element geometry, DOE, and speed differential between rolls in different nips.

Figure 16A:
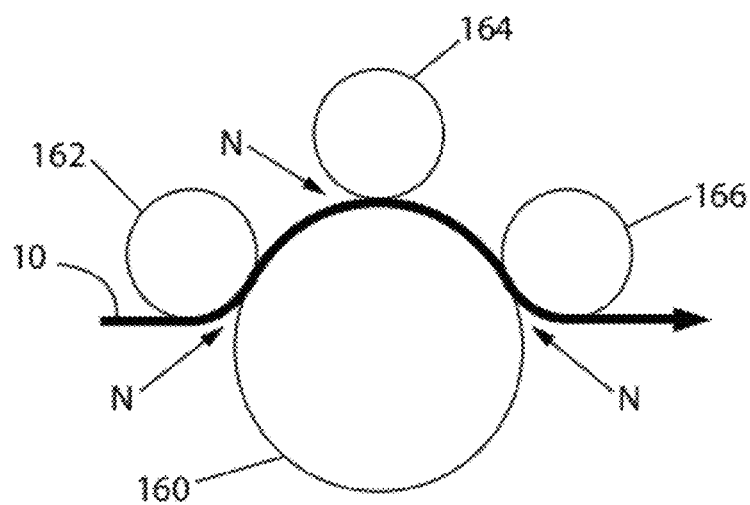
FIG. 16A is a schematic side view of another embodiment of an apparatus for making an absorbent member.

FIG. 16A is another embodiment of an apparatus for making an absorbent member. The apparatus shown in FIG. 16A has a planetary configuration which comprises a central roll 160 and satellite rolls 162, 164, and 166 that form multiple nips on the central roll 160. In this roll arrangement, at least one of the satellite rolls may be operating at a speed differential with respect to the central roll. The other satellite rolls may either be operating at a differential speed, or at a matched speed, with respect to the central roll.

2. Density Reduction Methods Utilizing Combinations of at Least One Differential Speed Nip and Matched Speed Nip(s).

As discussed above, variations of the methods described herein may utilize multiple nips that may comprise at least one differential speed nip, and at least one matched speed nip. The phrases "substantially the same speed" and "matched speed", as used herein, are synonymous, and mean that there is less than a 1.01 speed ratio between the rolls or other forming members. The speed of the rolls is measured in terms of surface or peripheral speed. In some cases, it may be desirable for there to be multiple matched speed nips. The forming members that form the matched speed nips may be arranged in a number of different configurations. The differential speed nip(s) and the matched speed nips may be arranged in any order (with either taking place first).

It has been found that the differential speed process can provide the precursor web with a much greater increase in bulk and flexibility in fewer nips than can be achieved with the matched speed process alone. The additional matched speed rolls may be used to further decrease the surface density of the formed web, increase the flexibility, or to provide the web with other properties that could otherwise not be achieved with the differential speed process alone. Therefore, a combination of the differential speed and matched speed rolls can provide all of the desired properties with the fewest number of nips.

Figure 17:
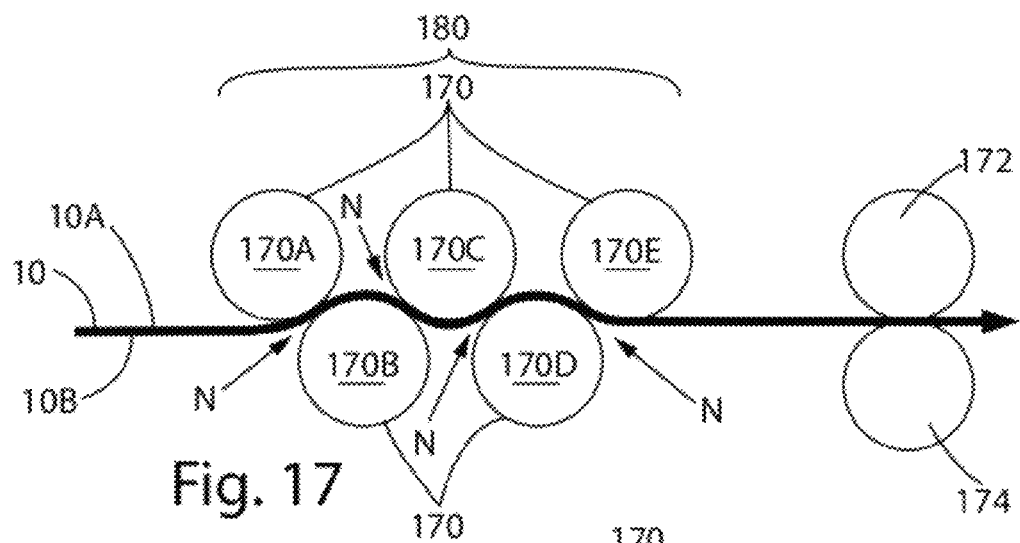
FIG. 17 is a schematic view of a variation of an apparatus having optional additional rolls located upstream of the differential speed nip.
Figure 18:
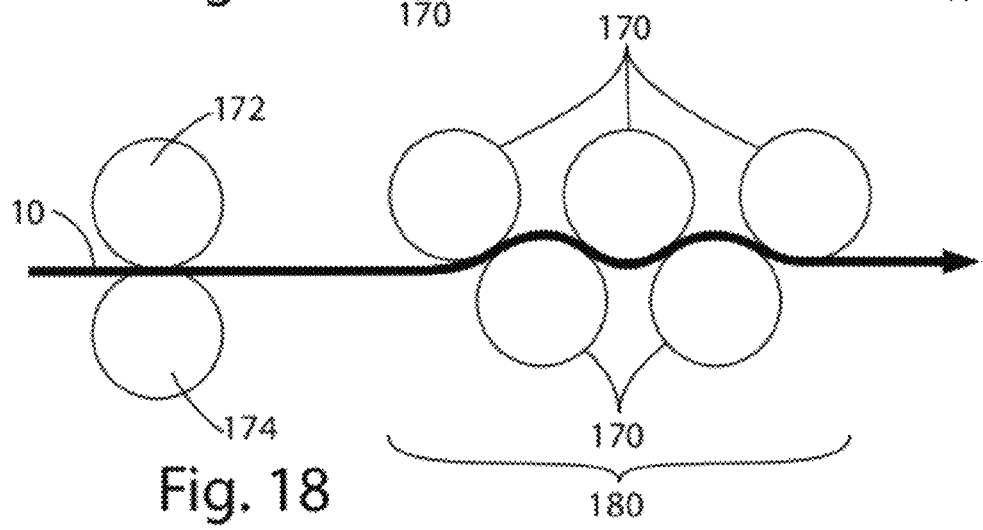
FIG. 18 is a schematic view of a variation of an apparatus having optional additional rolls located downstream of the differential speed nip.

The optional additional matched speed rolls may provide a nip that is located: (1) before or upstream of the rolls that are rotating at a speed differential (as shown in FIG. 17); (2) between the rolls that are rotating at a speed differential (if there are more than one pair of rolls that are rotating at a speed differential); (3) after or downstream of the rolls that are rotating at a speed differential (as shown in FIG. 18); or, (4) any combination thereof.

The surface of the additional matched speed rolls 170 may, depending on the desired type of mechanical deformation, be: substantially smooth (i.e., an anvil roll); or, provided with forming elements comprising protrusions or "male" elements, so long as each nip comprises at least one roll with discrete male forming elements. For rolls having surfaces with ridges and grooves thereon, the ridges are considered to be male forming elements. Male elements may be discrete (such as SELF teeth, pins, or RKA teeth) or continuous (such as the ridges on a ring roll). In some embodiments, the components of the forming structure may be substantially free of, or completely free of combinations of discrete male and mating discrete female elements such as those that would be used for embossing.

There can be any suitable number of additional rolls that form any suitable number of additional nips therebetween. The number of matched speed nips to which the precursor web is subjected can range from one to between 2 and 100, or more, nips. In some cases, for example, it may be desirable to run the precursor web 10 through as many as thirty or more nips. In order to run the precursor web 10 through thirty nips, if the rolls are arranged in a paired configuration, there would have to be thirty pairs of rolls.

However, such roll arrangements are less than optimal since so many rolls are required, and the large number of rolls will occupy an excessive amount of space on a manufacturing floor. Therefore, applicants have developed improved configurations for arrangement of the rolls. The rolls can, depending on the embodiment, be arranged in any suitable configuration when viewed from the side, including: paired (FIG. 16); planetary (FIG. 16A); nested configurations (part of the apparatuses shown in FIGS. 17 and 18); and combinations of such configurations (hybrid) (FIGS. 17 and 18). These roll configurations are described in greater detail in U.S. patent application Ser. No. 13/094,206 filed on Apr. 26, 2011.

The portion 180 of the apparatus shown on the left side of FIG. 17 (and on the right side of FIG. 18) will be referred to as a "nested roll" arrangement. In the nested roll portion of the apparatus, the rolls 170 are arranged in an offset configuration when viewed from their sides (that is, their ends) in which one roll, such as rolls 170B, 170C, and 170D, is positioned in a gap between two adjacent rolls so that at least two of the rolls define two or more nips N thereon with other rolls. Typically, in a nested roll arrangement, there will be at least four generally cylindrical rolls.

The nested roll arrangement may provide several advantages. A nested roll arrangement may provide more nips per total number of rolls than non-nested roll arrangements. This results in the need for substantially less tooling (machined rolls) than in the paired roll apparatus. The nested roll arrangement maintains better control of the web for registering deformations in the web since all portions of the web remain in contact with at least one of the rolls from the point where the web enters the first nip to the location where the web exits the last nip. The nested roll arrangement also has a smaller footprint on a manufacturing floor. The entire nested roll arrangement shown in FIGS. 17 and 18, for example, could also be rotated 90° so that the rolls are stacked vertically, and the apparatus would occupy even less space on a manufacturing floor.

Figure 19:
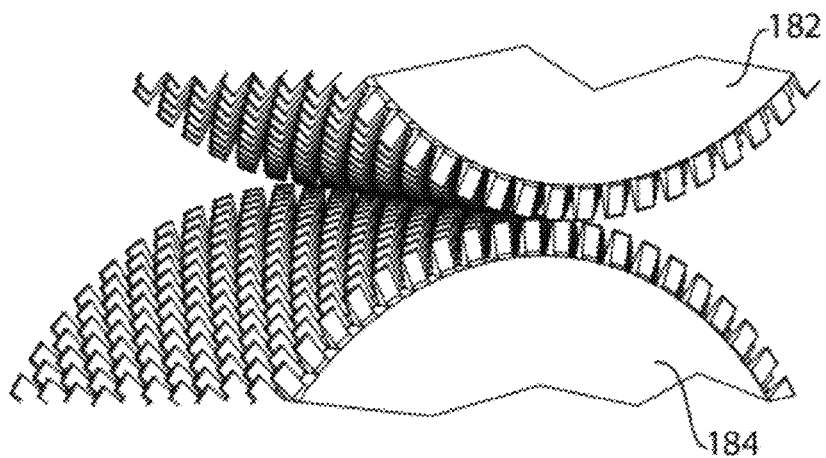
FIG. 19 is an enlarged perspective view of a portion of two intermeshing rolls.

FIG. 19 is a close up of one non-limiting embodiment of the surfaces of two matched speed rolls 182 and 184. The rolls 182 and 184 are carried on respective rotatable shafts (not shown) having their axes of rotation disposed in a parallel relationship. In this embodiment, each of the rolls 182 and 184 comprises a variation of one of the Procter & Gamble Company's SELF technology rolls. In this embodiment, the forming elements (or teeth) on the SELF rolls have their longer dimension oriented in the machine direction (MD). As shown in FIG. 19, the DOE may be less than that of the rolls that rotate at a differential speed such as that shown in FIG. 5. Often, the DOE of the matched speed rolls is less than the thickness of the precursor web, or even negative (in which there is an open gap between the rolls such that the rolls are not intermeshing). The examples in the table below represent examples of settings for the matched speed portion of the processes, showing the ratio of thickness to DOE is typically equal to or greater than 1. For negative DOE values, the ratio of thickness to DOE is obtained by dividing the thickness by the absolute value of the DOE.

| Material | Material Thickness (inches/mm) | DOE (inches/mm) | Ratio of Thickness to DOE |
|---|---|---|---|
| Drylap 200 gsm | 0.020/0.51 | 0.015/0.38 | 1.3 |
| Drylap 680 gsm | 0.060/1.5 | 0.001/0.025 | 60 |

FIG. 20 is a further enlarged view of several inter-engaged teeth 50 and 52 and grooves 54 of rolls with a web 10 of material therebetween. As shown, a portion of a web 10, which can be precursor web such as shown in FIG. 1, is received between the inter-engaged teeth 50 and 52, and grooves 54 of the respective rolls. The inter-engagement of the teeth 50 and 52 and grooves 54 of the rolls causes laterally-spaced portions 12 of web 10 to be pressed by teeth 50 and 52 into opposed grooves 54. In the course of passing between matched speed forming rolls, the web bends around the teeth 50 and 52, inducing shear forces in the web that result in the selective breakage and preservation of hydrogen bonds and disentanglement of the fibers. As shown in FIG. 20, the teeth 50 and 52 are not required to penetrate through the entire thickness of the precursor web 10.

In general, to obtain the greatest amount of de-densification in the fewest number of hits, while preserving a portion of the integrity of the web, it may be desirable to have a short tooth length TL and a small tip radius TR to maximize the amount of bending around the tooth and minimize the amount of compression on the material. Thus, it may be desirable for the tooth tip radius TR to be less than 0.020 inch (about 0.5 mm). However, this must be balanced with the need to have a tooth that will not easily break when the force from the deformation is applied. The tooth spacing TD between the teeth should be large enough to enable the material to bend around the leading and trailing edges, LE and TE, respectively, of the teeth. If the TD is too small, the material will bridge the gap between the teeth and the amount of de-densification will be lower. The optimum pitch of the teeth depends on the thickness of the precursor material 10, and is typically around two times the thickness of the web 10. If the pitch P is too small, the material 10 will remain fairly dense after multiple passes. If the pitch P is too high, the CD spacing between the teeth after the rolls are mated together will be greater than the thickness of the web 10 and the teeth will not sufficiently create shear between the layers of the web, which is required to selectively break the hydrogen bonds.

The teeth described herein may have a smaller tip radius TR than the male elements used in typical embossing processes to ensure the amount of compaction of the material 10 is minimized as the material is being bent over the teeth. Also, unlike embossing, the clearance between the teeth, or the shortest distance D between the tips of the teeth of the tooling described herein, may be smaller than the thickness of the web 10 to induce additional shear forces in the web. This results in a greater amount of de-densification of the material because hydrogen bonds are not only broken on the outer surfaces of the web but also may be broken inward of the outer surfaces of the web.

Because of the localized cross-web stretching of the web 10 that has taken place, with the consequent increase in web width, the web material that exits from the matched speed forming rolls can have a lower basis weight than that of the entering web material, provided the exiting material remains in a substantially flat, laterally extended state. The resulting modified web can have a web width that can range from about 100% to about 150% of the initial web width and a basis weight that is less than or equal to the web's original basis weight.

The rolls forming the matched speed nip(s) described above may be configured to provide the precursor web with various reduced density properties before it is subjected to the differential speed process to create an absorbent member, thus forming an "intermediate precursor web" 15. The intermediate precursor web may have reduced density zones on each side of the precursor web (a "two side de-densified" intermediate precursor web 15); or, a reduced density zone on one side of the precursor web (a "one side de-densified" intermediate precursor web 15). The forming members used in the matched speed nip(s) may also be configured to provide an intermediate precursor web 15 with X-Y regions that are: two side de-densified; one side de-densified; and/or not de-densified.

i. Two Side De-Densified Precursor Webs.

In one variation of the process shown in FIG. 17, the additional matched speed rolls can be configured to reduce the density on both sides of the precursor web (that is, to provide a two-side de-densified intermediate precursor web).

Figure 21:
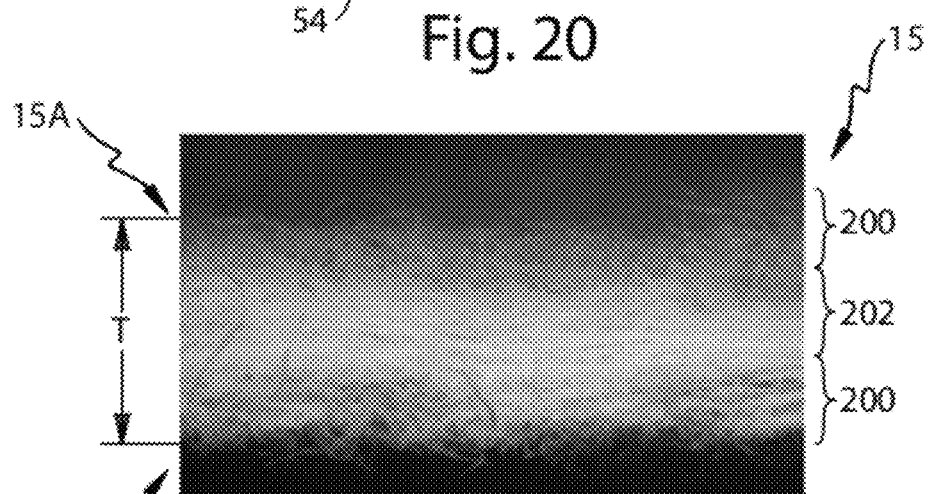
FIG. 21 is a photomicrograph of the cross-section of a web of dry lap after it has been processed according to one embodiment of the present method to form a two-side de-densified precursor web.

The apparatus shown in FIG. 19 is one example of an apparatus for making a two side de-densified intermediate precursor web 15 such as that shown in FIG. 21. To form an intermediate precursor web 15 which has a lower density portion 200 on both sides 15A and 15B, and a higher density region 202 in between, both of the components 170 of the forming structure (such as both of the rolls in at least one nip) should have forming elements on their surfaces. Suitable configurations for the forming elements include, but are not limited to: SELF rolls; Micro-SELF rolls; pin rolls; and RKA rolls. In the embodiment shown, each of the rolls 170 comprises one of the Procter & Gamble Company's staggered CD SELF technology rolls. In this embodiment, the forming elements (or teeth) on the SELF rolls have their longer dimension oriented in the machine direction (MD).

For making an intermediate precursor web 15 such as that shown in FIG. 21 from a precursor web 10 having a basis weight in the range of from about 200 to 700 gsm, the teeth may have a length TL ranging from about 0.5 mm (0.020 inch), or less, to about 10 mm (0.400 inch), alternatively from about 1 mm (0.040 inch) to about 3 mm (0.120 inch), and a spacing TD from about 0.5 mm (0.020 inch) to about 10 mm (0.400 inch), alternatively from about 1 mm (0.040 inch) to about 3 mm (0.120 inch), a tooth height TH ranging from about 0.5 mm (0.020 inch) to about 10 mm (0.400 inch), alternatively from about 2 mm (0.080 inch) to about 5 mm (0.200 inch), a tooth tip radius TR ranging from about 0.05 mm (0.002 inch) to about 0.5 mm (0.020 inch), alternatively from about 0.1 mm (0.004 inch) to about 0.5 mm (0.020), and a pitch P between about 1 mm (0.040 inches) and 10 mm (0.400 inches), alternatively from about 1.5 mm (0.060 inch) to about 3 mm (0.120 inch). The depth of engagement DOE can be from about −1 mm (−0.040 inch) to about 5 mm (0.200 inch) (up to a maximum approaching the tooth height TH). Of course, E, P, TH, TD, TL, and TR can each be varied independently of each other to achieve the desired properties in the intermediate precursor web 15. In one embodiment of roll useful for making an intermediate precursor web 15 such as that shown in FIG. 21, the teeth have a uniform circumferential length dimension TL of about 0.080 inch (2 mm), a tooth tip radius TR at the tooth tip of about 0.005 inch (0.13 mm), are uniformly spaced from one another circumferentially by a distance TD of about 0.080 inch (2 mm), have a tooth height TH of 0.138 inch (3.5 mm), have a tooth side wall angle of about 8.5 degrees (measured from the base of the tooth to near the tip of the tooth, before the formation of the radius), and a have a pitch of about 0.080 inch (2 mm). The clearance between the teeth of mating rolls, if plotted, varies linearly with the depth of engagement. For this embodiment, the clearance of the teeth for non-meshing rolls at −0.010 inch (0.25 mm) depth of engagement is 0.034 inch (0.86 mm) and the clearance for meshing rolls at 0.015 inch (0.38 mm) depth of engagement is 0.029 inch (0.74 mm).

ii. One Side De-Densified Precursor Webs.

In another variation of the process shown in FIG. 17, the additional matched speed rolls can be configured to reduce the density primarily one side of the precursor web. In the methods for making a one-side de-densified intermediate precursor web 15, the precursor web 10 is subjected to multiple passes through a nip formed between rolls having discrete forming elements thereon and opposing rolls that have a relatively smoother surface pattern.

Figure 22:
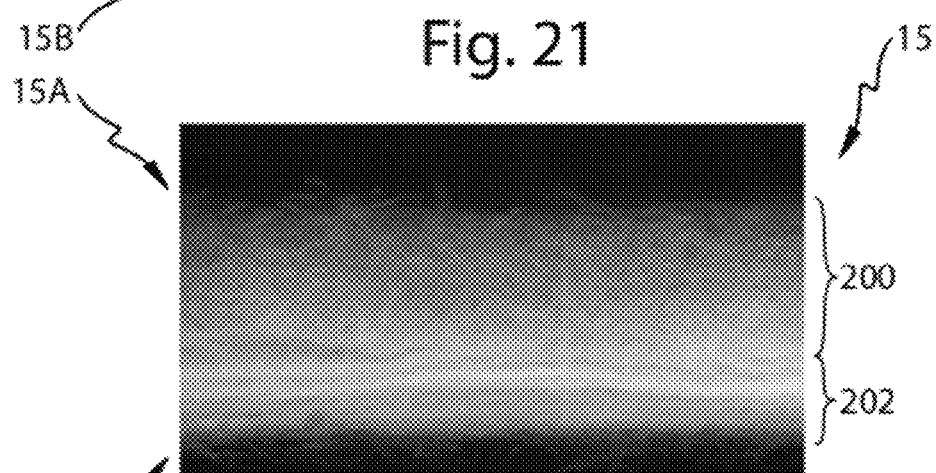
FIG. 22 is a photomicrograph of the cross-section of a web of dry lap after it has been processed according to another embodiment of the present method to form a one-side "de-densified" precursor web.

In this case, the apparatus is used for making a one side de-densified intermediate precursor web 15 such as that shown in FIG. 22. In this embodiment, the apparatus provides a plurality of nips N between rolls that have forming elements thereon, and opposing rolls that have a relatively smoother surface pattern. For example, the nested roll portion of the apparatus has rolls 170A, 170C, and 170E on a first side 10A of the precursor web 10 that have forming elements thereon, and the rolls 170B and 170D on the second side 10B of the precursor web 10 have a relatively smoother surface pattern. In the embodiment shown, each roll 170B and 170D having a relatively smoother surface pattern forms a nip N with two of the rolls having forming elements thereon. In such an embodiment, the rolls 170A, 170C, and 170E having forming elements thereon can comprise any suitable type of roll having discrete forming elements thereon including, but not limited to SELF rolls, pin rolls and RKA rolls. The rolls 170B and 170D with the relatively smooth surface can comprise any suitable type of roll having a smoother surface than that of the roll having forming elements thereon. The rolls 170B and 170D with the relatively smooth surface include, but are not limited to: flat anvil rolls, ring rolls; or, another SELF roll with a different, smoother pattern than the roll having forming elements thereon. In cases in which the rolls 170B and 170D with the relatively smooth surface comprise either a ring roll or a SELF roll, such a roll could have elements thereon with a smaller pitch than the roll having forming elements thereon, or a larger tip radius. In cases in which the rolls 170B and 170D with the relatively smooth surface comprise a SELF roll, such a roll could have elements thereon with longer teeth and/or smaller MD spacing between the teeth to make them more like ring rolls. In such an embodiment, the forming elements on said first forming member, rolls 170A, 170C, and 170E having forming elements thereon penetrate into the first surface 10A of said precursor web material 10 only part of the way into the thickness of the precursor web material, and the second surface 10B of said precursor web material is in contact with the surface of the rolls 170B and 170D with the relatively smooth surface.

FIG. 22 shows a web of dry lap after it has been run through a plurality of matched speed nips in order to form a skewed or "one-side de-densified" intermediate precursor web 15. As shown in FIG. 22, the intermediate precursor web 15 comprises a unitary absorbent fibrous layer having a higher density zone 202 adjacent one side 15B of the precursor web and a lower density zone 200 adjacent another side 15A of the precursor web. The lower density portion 200 may provide the absorbent member with increased void volume for faster liquid acquisition. The higher and lower density zones may comprise a significant portion of the overall thickness of the absorbent member.

The above method variations allow a density profile to be provided in a unitary structure which eliminates the need to provide separate layers having different properties and bonding such layers together. This can eliminate a bonding step during processing, and eliminate the need for adhesives or other materials to hold separate layers together (which adhesives may interfere with the transportation of liquids between layers).

Figure 23:
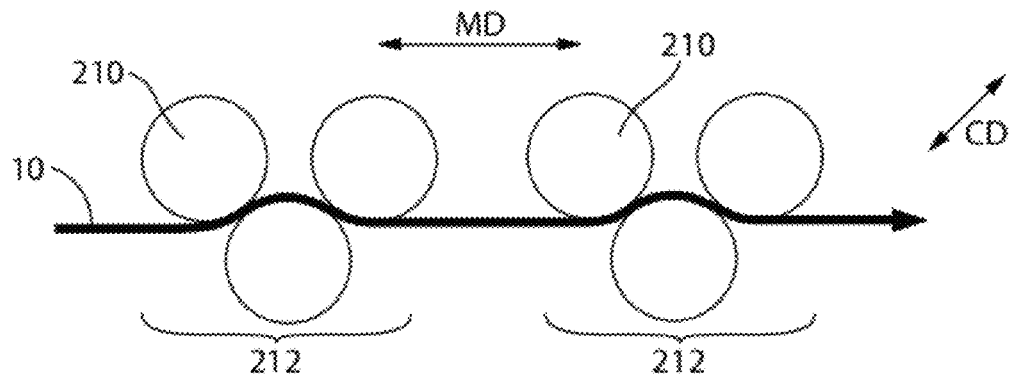
FIG. 23 is a schematic side view of another embodiment of an apparatus for making an absorbent member.

Numerous variations of the operation of the forming members in the matched speed nips described herein are possible. The processes described herein can be configured and controlled to locally bend the precursor material 10 in opposite directions in the same location across the surface of the web when the web passes from one nip to another. The apparatus can also be configured and controlled to locally bend the precursor material 10 in different locations across the surface of the web when the web passes from one nip to another. It is desirable for the rolls to be patterned and arranged such that the precursor material is deformed in the greatest number of different locations on the surface before exiting the process, and so that this is accomplished in the fewest number of hits and/or in the smallest process footprint. The rolls can have staggered or standard patterns. The rolls can be aligned or mis-aligned relative to each other in the MD and/or CD. The rolls may all have the same SELF pattern thereon, or the pattern on the rolls and/or DOE can vary between rolls (that is, for each pass through a nip). The desired DOE for each pass depends on caliper of the precursor material at each pass. An example of an apparatus that maximizes the de-densification of the material 10 in a small process footprint is shown in FIG. 23. As shown in FIG. 23, the apparatus includes rolls 210 arranged in a hybrid arrangement such that there are multiple three roll clusters 212 that are then off-set relative to each other in the CD.

C. Pre-Processing and/or Post-Processing.

Figure 24:
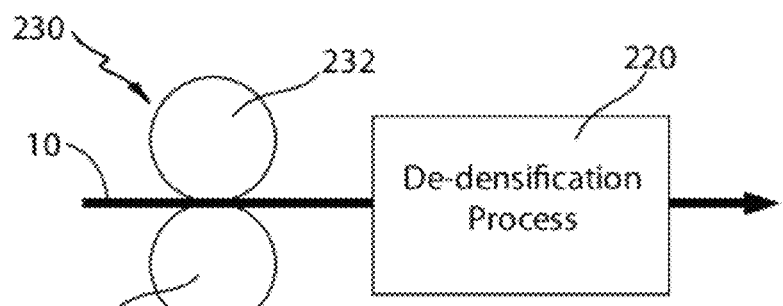
FIG. 24 is a schematic diagram of another embodiment of an apparatus for making an absorbent member.
Figure 25:
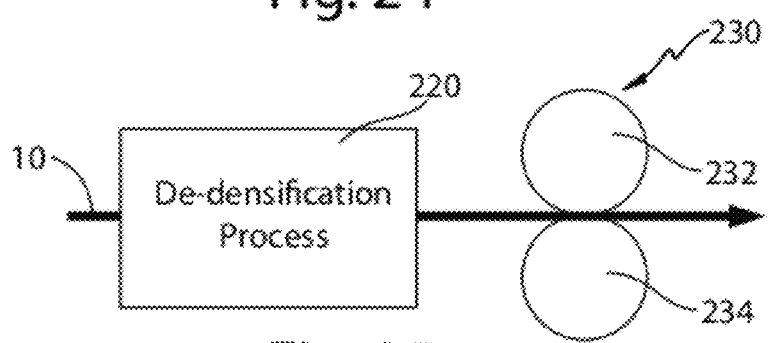
FIG. 25 is a schematic diagram of another embodiment of an apparatus for making an absorbent member.

In other embodiments, apparatuses such as that shown in FIGS. 24 and 25 can be used to pre- and/or post-process the precursor material 10 before and/or after it is passed through the de-densification process. In FIGS. 24 and 25, the de-densification process is represented schematically by block 220. The de-densification process 220 can, as described above, include at least one set of differential speed forming members, but could also include matched speed forming members. These apparatuses further comprise forming members, such as rolls 232 and 234 that form an additional forming station 230. In such case, the forming members forming the additional nip may rotate at substantially the same speed, rather than at a speed differential.

These additional pre- and/or post-processing steps can be used to form absorbent members with the properties which include, but are not limited to: (1) re-densified or compacted versions of the absorbent members; (2) absorbent members having a three dimensional (3D) topography; (3) apertured version of the absorbent members; and (4) alternative embodiments and combinations of any of the foregoing types of absorbent members. Each of these methods and types of absorbent members are described in greater detail below.

1. Methods for Forming Compacted Absorbent Members.

Figure 26:
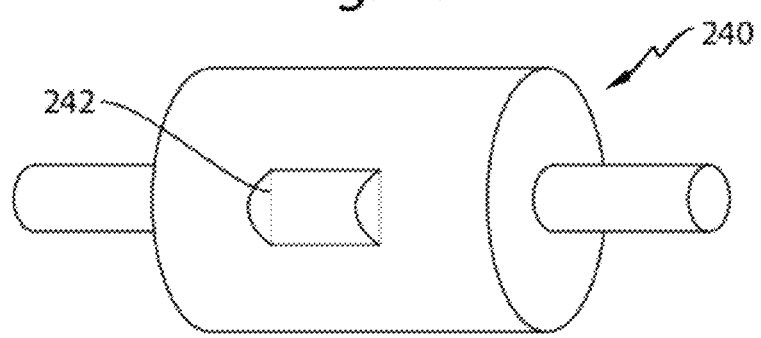
FIG. 26 shows one non-limiting example of a forming member for an optional step of forming the precursor web into an absorbent member wherein a portion of the absorbent member has been re-densified or compacted.

In some embodiments, the precursor material is de-densified such as described above, and at least a region of the surface area of the material is then compacted. This compaction step may be done to increase the capillary suction of the material or increase the stiffness of the material in at least select regions. The de-densified absorbent member can be compacted (or "re-densified") over its entire surface, or at least one region thereof. FIG. 26 shows one non-limiting example of a forming member 240 for the step of forming the precursor web 10 into an absorbent member with different density regions. As shown in FIG. 26, the forming member 240 comprises a roll having a raised region 242 thereon for compacting the de-densified absorbent material only in select areas/regions in the x-y plane. The process may be aided by misting the web prior to the compaction step to provide an increased level of compaction or more permanent compaction of the web.

Figure 27:
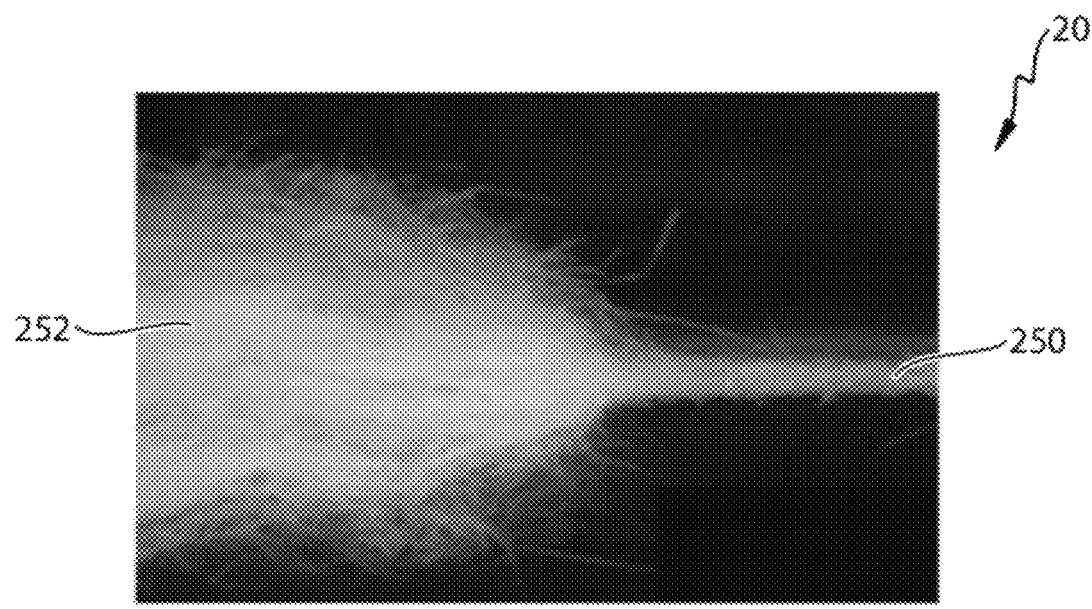
FIG. 27 is a photomicrograph of the cross-section of an absorbent member, a portion of which has been compacted.

FIG. 27 shows an example of a compacted web. As shown in FIG. 27, the absorbent member 20 has a region 250 thereof, on the right side of the image, which has been re-densified or compacted. The region 252 of the absorbent member 20 on the left side of FIG. 27 has not been compacted and remains de-densified. In other embodiments, the entire absorbent member 20 may be re-densified or compacted. Absorbent members having a re-densified or compacted density profile can be useful in that thinness may provide discretion, which is important for some consumers. In a re-densified or compacted absorbent member, the majority of the improvement in flexibility of the de-densified absorbent member can be retained if the compaction level is not too high.

2. Methods of Providing the Absorbent Member with a Three Dimensional Topography.

In other embodiments, the absorbent member can be provided with a three dimensional topography (that is in addition to any 3D topography formed by the differential speed rolls). In such embodiments, at least one of the first surface and second surface of the absorbent member 20 may be provided with additional (and is some cases larger) protrusions and/or depressions. Providing the absorbent member with a three dimensional topography not only changes the topography of the web, but, in some cases, further increases the caliper/bulk of the web.

The method of providing a three dimensional absorbent member involves subjecting the precursor web to a process for forming a three dimensional structure into the precursor web before and/or after it is de-densified as described above. The method of making a three dimensional absorbent member, thus, may involve first de-densifying a precursor web material, such as by using one of apparatuses described above. The de-densified absorbent material is then subjected to a further mechanical deformation step, such as shown in FIG. 25, using forming members having forming elements thereon and moving at substantially equal surface speeds. The de-densified absorbent material can be subjected to a further mechanical deformation step in any suitable manner. Alternatively, as in the case of FIG. 24, the precursor web material 10 could first be subjected to a mechanical deformation step using forming members having forming elements thereon, moving at substantially equal surface speeds, and then de-densified using one of the approaches described above.

Figure 30:
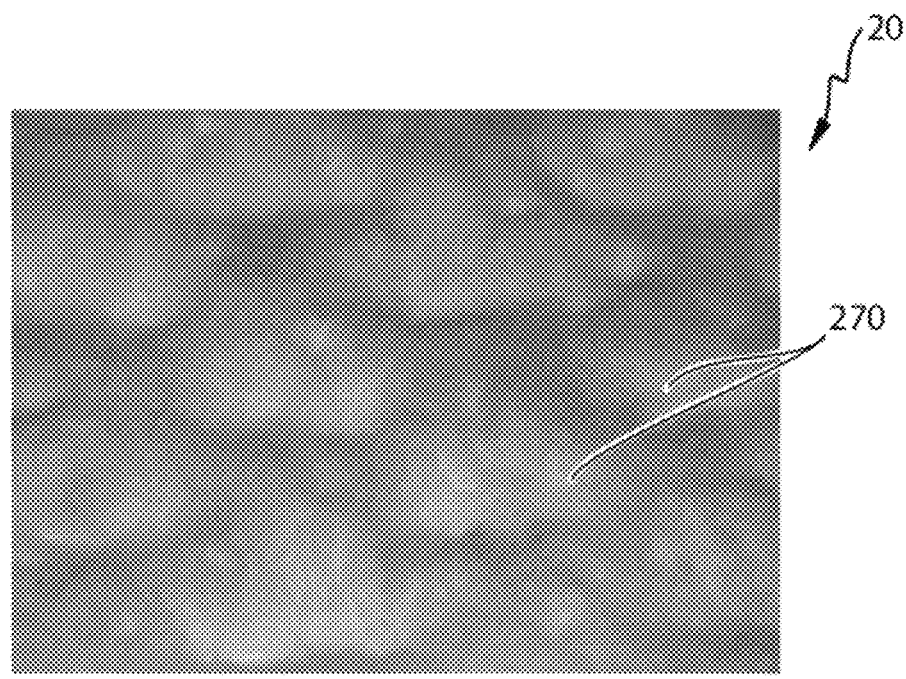
FIG. 30 is a top perspective view photograph of an absorbent member with a three dimensional topography.

FIG. 25 schematically shows one non-limiting embodiment of an apparatus for making a three-dimensional absorbent member 20 having protrusions 270, such as shown in FIG. 30. The de-densification portion 220 of the apparatus may comprise a first differential speed nip comprising two rolls similar to those shown in FIG. 5, 12, or 13 with un-equal surface speeds, and the additional forming station 230 may comprise a three-dimensional forming nip with rolls rotating at substantially the same surface speed. In alternative embodiments, such as shown in FIG. 24, the precursor web 10 can be passed through the three-dimensional forming station and then fed through a de-densification process.

The three-dimensional forming station can comprise any suitable combination of forming members that are capable of imparting a three-dimensional texture to the precursor web 10 and move or rotate at substantially the same surface speed. At least one of the forming members, which will be referred to as the three-dimensional forming member, should have male elements thereon. Such rolls could include, for example, a SELF roll (CD or MD SELF). Several examples of three-dimensional forming rolls are described below. The direction of the ridges or teeth on the opposing roll should be the same as that on the three-dimensional forming roll. The depth of engagement of the elements on the three-dimensional forming roll with the forming elements on the opposing roll is typically at least 0.04 inch (1 mm) or more in order to impart a significant amount of topography into the web. Any roll satisfying the above requirements can be used as the opposing roll. The opposing roll can, for example, be either a ring roll or a SELF roll.

Figure 28:
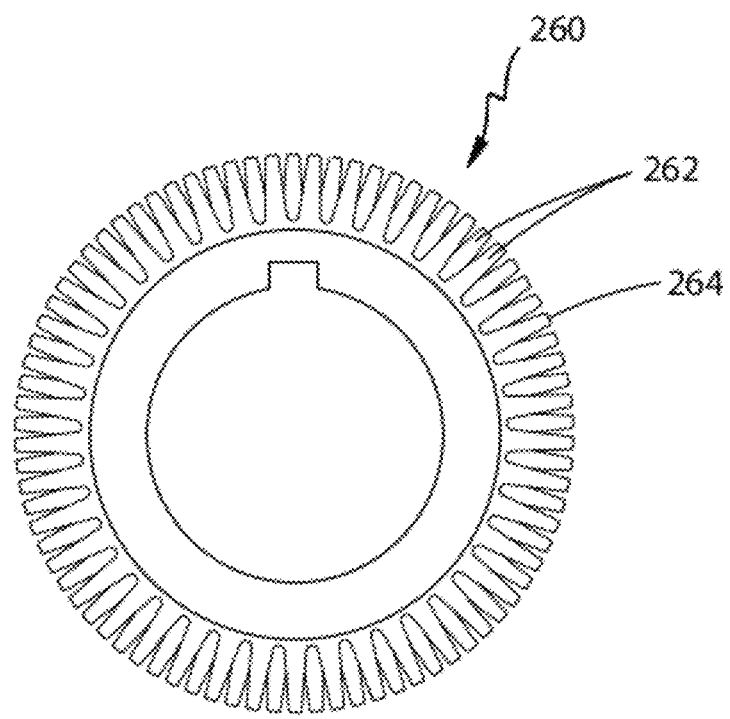
FIG. 28 is a schematic side view of one non-limiting example of a forming member for an optional step of forming the precursor web into a three dimensional absorbent member.

FIG. 28 shows one non-limiting example of a three dimensional forming roll 260 for the step of forming the precursor web 10 into a three dimensional absorbent member. As shown in FIG. 28, the forming roll 260 comprises a CD SELF roll in which the teeth 262 are oriented in the machine direction, and are staggered. In the embodiment shown in FIG. 28, the tips 264 of the teeth 262 are concave. FIG. 29 shows another example of a forming member 80 for the step of forming the precursor web 10 into a three dimensional absorbent member. As shown in FIG. 29, the forming member 80 comprises an MD SELF roll in which the teeth 82 are oriented in the CD and are staggered. The roll 80 has spaced apart channels 88 formed therein that are oriented around the circumference of the roll. Examples of suitable forming element (or tooth) dimensions and DOEs for the rolls shown in FIGS. 28 and 29 are provided below. The forming elements on the opposing ring roll or SELF roll may have the same pitch as the rolls described below.

|  | CD SELF | MD SELF |
| --- | --- | --- |
| Pattern | Staggered | Staggered |
| Pitch | 0.200 in. (5.0 mm) | 0.185 in. (4.6 mm) |
| Tooth length | 0.118 in. (3.0 mm) | 0.250 in. (6.4 mm) |
| Tooth spacing | 0.328 in. (8.3 mm) | 0.250 in. (6.4 mm) |
| Tip radius | 0.010 in. (0.25 mm) | 0.010 in. (0.25 mm) |
| Tip shape | Concave | Flat |
| DOE for 3D samples | 0.105 in. (2.7 mm) | 0.090 in. (2.3 mm) |

3. Method for Making Apertured Absorbent Members.

In other embodiments, the absorbent member can be apertured. The method of making an apertured absorbent member involves aperturing a precursor web material before and/or after de-densifying the precursor web material. The apparatus for making an apertured absorbent member may, thus, utilize an arrangement similar to that shown in FIG. 24 or 25. In one example, the de-densification step may be carried out by two rolls similar to those shown in FIG. 5, 12, or 13 with un-equal surface speeds, and the aperturing step is formed by an aperturing apparatus.

Figure 31:
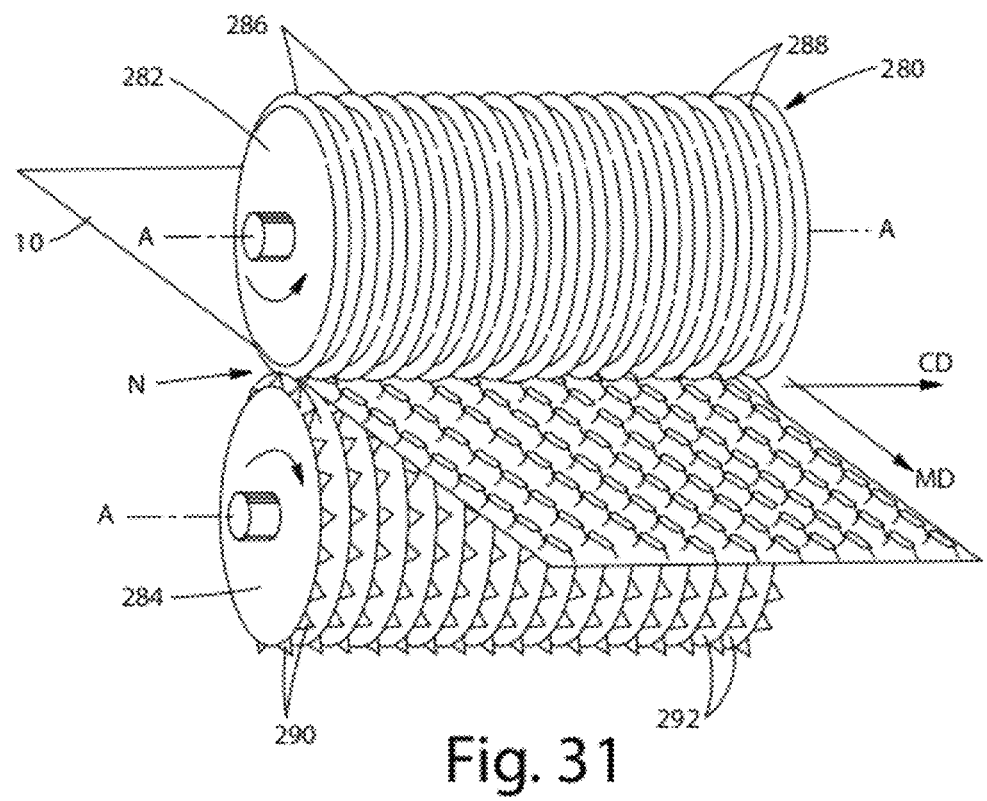
FIG. 31 is a perspective view of two intermeshing rolls that may be used to form an apertured absorbent member.

The precursor web 10 can be apertured in any suitable manner. Any aperturing processes known in the art can be used including, but not limited to: a die punch or RKA rolls. The precursor web 10 can be apertured over its entire surface or in regions. FIG. 31 shows one non-limiting example of an aperturing station 280 for the step of forming the precursor web 10 into an apertured absorbent member. As shown in FIG. 31, aperturing station 280 comprises a pair of counter-rotating, intermeshing rollers, wherein the top roll 282 is a ring roll, and the bottom roll 284 is a Rotary Knife Aperturing (or "RKA") roll. As shown in FIG. 31, the top ring roll 282 comprises circumferentially-extending ridges 286 and grooves 288. The bottom roll 284 comprises circumferentially-extending alternating rows of teeth 290 and grooves 292. The teeth 290 are joined to the bottom roll at their bases. The teeth 290 are tapered from their base to their tip, and the base of the teeth have a cross-sectional length dimension greater than a cross-sectional width dimension. Apertures are formed in the web material 10 as the teeth on the RKA roll intermesh with grooves on the ring roll 282. RKA rolls are described in greater detail in U.S. Patent Application Publication No. US 2006/0087053 A1.

D. Other Process Features.

Numerous alternative embodiments and combinations of the foregoing methods are possible. For instance, a precursor web can be fed through the apparatuses described herein any number of times, and the web can be thereafter fed through another one of the apparatuses any number of times. In addition, more than one absorbent member and/or other materials can be combined to form still other absorbent structures, and these laminates can be fed together through any of the apparatuses described herein.

The apparatus for de-densifying the precursor material can be provided at any suitable location, or stage, in the process of manufacturing an absorbent article. In some embodiments, the method can serve as a pre-processing step prior to feeding the precursor material into a hammer mill in order to reduce the energy required to defibrillate the material in the hammer mill. In other embodiments, the method and apparatus can be provided instead of a hammer mill at a location apart from an absorbent article manufacturing line, such as at the location formerly occupied by the hammer mill. In still other embodiments, instead of being in a separate location from the absorbent article manufacturing line, the apparatus for de-densifying dry lap can be located as a unit operation at or near the beginning (or at some other convenient location) of an absorbent article manufacturing line in order to prepare a completed absorbent member that is ready for use in an absorbent article being made on the line.

It may be desirable to make the width of the roll of precursor material equal to the width or length of the absorbent core, or other structure desired to be formed so that the roll of absorbent member material can be conveniently cut into individual cores.

The process described above, thus, may use an apparatus that has male elements on opposing surfaces in contrast to embossing apparatuses that employ male elements on one surface and female elements within which the male elements fit, on an opposing surface. In addition, in the present process, the clearance between the elements may be less than the thickness of the web. This may be used to apply increased shear forces on the web (in contrast to apparatuses that require that the clearance between elements be greater than or equal to that of the web being processed). The process described herein may be capable of not only breaking weak hydrogen bonds on the surface of the precursor material to soften the surface of the same, it may also selectively break the stronger hydrogen bonds and those bonds towards the interior of the material and significantly de-densify and weaken the web. It can also be used to significantly increase the caliper (measured under load) of the precursor web. The structure of precursor web can be preserved in certain zones for strength while hydrogen bonds can be broken in other zones for acquisition.

IV. Examples

TABLE 1

Drylap Precursor and Mechanically Deformed Materials

| | 400 gsm Drylap | Ex. 1 | Ex. 2 | Ex. 3 | Ex. 4 | Ex. 5 1st step | Ex. 5 2nd step |
|---|---|---|---|---|---|---|---|
| Tooling | — | 100 pitch RKA mated to Shark Fin | 100 pitch RKA mated to Shark Fin | 100 pitch RKA mated to Shark Fin | 80 pitch SELF mated to SELF | 80 pitch SELF mated to SELF | 100 pitch RKA mated to Shark Fin |
| Surface Speed Ratio | — | 1.19 | 1.31 | 1.31 | 1.06 | 0 | 1.31 |
| Number of Passes | — | 1 | 1 | 1 | 1 | 4 | 1 |
| DOE (inches) | — | 0.080 | 0.080 | 0.115 | 0.042 | 0.015 | 0.075 |
| Caliper (mm) | 1.0 | 3.9 | 4.5 | 4.9 | 3.1 | — | 4.1 |
| Basis Weight (g/m$^2$) | 392.1 | 389.1 | 418.4 | 418.2 | 400.9 | — | 416.2 |
| Bulk Density (g/cm$^3$) | 0.39 | 0.10 | 0.093 | 0.085 | 0.13 | — | 0.10 |
| CD Peak Tensile (N) | 158.9 | 16.7 | 33.6 | 4.7 | 12.3 | — | 4.1 |
| MD Peak Tensile (N) | 263.9 | 18.9 | 27.6 | 4.5 | 16.3 | — | 5.1 |

Examples 1-3 in Table 1 above represent samples of 400 gsm drylap, also in the table above, mechanically deformed according to the present invention. For each of the examples, a web of drylap approximately 80 millimeters wide is processed at approximately 1,000 feet per minute (305 meters/minute) using the tooling, depth of engagement DOE and surface speed ratio listed in Table 1 above.

The shark fin roll is similar to that shown in FIG. 9. The teeth are arranged in a staggered pattern and are oriented so the long direction runs in the MD. The teeth have a CD pitch P of 0.100 inch (2.5 mm) and a uniform tip to tip spacing in the MD of 0.414 inch (10.5 mm). The base of the shark fin tooth is shaped like a hexagon, with a length TL of 0.238 inches (6.0 mm). The tooth height TH is 0.291 inches (7.4 mm). The side walls of the tooth have a 10 degree included angle (i.e., each side wall is angled 5 degrees from vertical). The tooth has a pointed tip and all six sides of the tooth taper at a constant angle from the base of the tooth to the tooth tip. The shark fin is oriented as shown in FIG. 12, with the leading edge LE of the tooth forming a larger angle with the base of the roll than the trailing edge TE. The leading edge LE of the tooth forms a 129 degree angle with the base of the roll and the trailing edge TE of the tooth forms a 90 degree angle with the base of the roll. The roll diameter is 5.69 inches (14.4 cm).

The roll mated to the shark fin roll is a staggered RKA roll, similar to that shown in FIG. 8. The teeth on the RKA roll are also arranged in a staggered pattern and are oriented so the long direction runs in the MD. The teeth have a CD pitch P of 0.100 inch (2.5 mm) and a uniform tip to tip spacing in the MD of 0.223 inch (5.7 mm). The base of the RKA tooth is shaped like a hexagon and has a tooth height TH of 0.270 inch (6.9 mm). The side walls of the tooth have a 13.6 degree included angle (i.e., each side wall is angled 6.8 degrees from vertical). The tooth has a pointed tip and the side walls of the tooth taper at a constant angle from the tooth tip to the base of the tooth. The leading edge LE and trailing edge TE of the tooth have a 50 degree included angle (i.e. each edge is angled 25 degrees from vertical). The walls that form the vertices that create the leading and trailing edges of the tooth taper at a constant angle from the tooth tip to a point on the tooth that is 0.170 inch (4.3 mm) below the tooth tip. Then, the walls change their angle to be vertical (i.e., at a 90 degree angle relative to the base of the roll) for the bottom 0.100" (2.54 mm) of the tooth. The RKA roll and shark fin roll are off-set relative to each other in the CD such that the clearances on either side of the teeth are about equal.

The position of the teeth on the shark fin and RKA rolls are not positioned in any specific manner in the MD. The surface speed of the RKA roll is slower than the surface speed of the shark fin roll by the surface speed ratio shown in the table. To create the surface speed ratio, the shark fin roll is run with a 36 tooth gear and the RKA roll is run with a 43 tooth gear (for 1.19 ratio in Ex. 1) and with a 47 tooth gear (for the 1.3 ratio in Ex. 2 and 3).

Example 4 in Table 1 above also represents a sample of 400 gsm drylap mechanically deformed according to the present invention. A web of drylap approximately 80 millimeters wide is processed at approximately 50 feet per minute (about 15 m/minute) using an SELF roll mated to an identical SELF roll, like that shown in FIG. 7, at 0.042 inch (1.07 mm) DOE. The first SELF roll is run on a 36 tooth gear, while the second SELF roll is run on a 38 tooth gear resulting in a 1.06 surface speed ratio between the two SELF rolls. The SELF rolls have a diameter of 5.6875 inches (14.4 cm). The SELF teeth have a uniform circumferential length dimension TL of about 0.080 inch (2 mm) measured generally from the leading edge LE to the trailing edge TE, a tooth tip radius TR at the tooth tip of about 0.005 inch (0.13 mm), are uniformly spaced from one another circumferentially by a distance TD of about 0.078 inch (2 mm), have a tooth height TH of 0.138 inch (3.5 mm), have a tooth side wall angle of about 8.5 degrees (measured from the base of the tooth to near the tip of the tooth, before the formation of the radius), and a have a pitch of about 0.080 inch (2 mm). The two SELF rolls are off-set relative to each other in the CD such that the clearances on either side of the teeth are about equal. The teeth on the two SELF rolls are not positioned in any specific manner in the MD.

Example 5 in Table 1 above also represents a sample of 400 gsm drylap mechanically deformed using multiple matched speed nips followed by a differential speed nip. A web of drylap approximately 80 millimeters wide is processed at approximately 50 feet per minute (about 15 m/minute) using a SELF roll mated to an identical SELF roll (described in Example 4 above) rotating at equal surface speeds at 0.015 inch (0.38 mm) DOE. The web is processed through the SELF tooling 4 times. Then, the web is processed in a subsequent step through an RKA roll mated to a shark fin roll (described in Examples 1-3 above) at 0.075" (1.9 mm) DOE. The shark fin roll is run on a 36 tooth gear, while the RKA roll is run on a 47 tooth gear, resulting in a 1.31 surface speed ratio with the shark fin roll rotating faster than the RKA roll. The RKA and shark fin rolls are off-set relative to each other in the CD such that the clearances on either side of the teeth are about equal. The teeth on the RKA and shark fin rolls are not positioned in any specific manner in the MD.

V. Test Methods

A. Caliper Method

Apparatus

The caliper of the material is quantified using a Thwing-Albert ProGage Thickness Tester or equivalent with a 56.4 millimeter diameter circular foot.

Number and Preparation of Specimens

A minimum of 3 representative samples are necessary to complete the testing. One specimen is cut from each of the 3 samples for a total of 3 test specimens. The specimen is cut from the center of the sample (e.g. centered on the intersection of the longitudinal and transverse centerlines). The portion of the specimen to be tested should only include the unitary absorbent member as defined by the specification. Therefore, the other materials that are not part of the absorbent member must be carefully removed such that the caliper of the material is not impacted. The specimens to be measured must be ≥65 millimeters in diameter to ensure the entire surface area of the foot comes in contact with the sample being measured.

Procedure

The test apparatus is always zeroed before any measurements are taken. The foot starts 0.5 inches above the surface on which the test specimen is placed and descends at a rate of 0.125 inches per second. When the foot reaches the target pressure of 0.51 kilopascals, it remains in contact with the specimen for 9 seconds while maintaining that pressure. The reading is taken at the end of the 9 second period.

Calculations

Each of the samples is individually measured and the average of the samples is reported to the nearest 0.01 millimeters.

B. Basis Weight Method

The Basis Weight is measured using a method based on Standard Test WSP 130.1, Standard Test Method for Mass Per Unit Area.

Apparatus

The weight of the material is quantified using a Mettler Toledo balance, model number AG245 or equivalent.

Number and Preparation of Specimens

A minimum of 3 representative samples are necessary to complete the testing. One specimen is cut from each of the 3 samples for a total of 3 test specimens. The specimens to be measured are cut to 50 mm×200 mm using a die. The specimen is cut from the center of the sample (e.g. centered on the intersection of the longitudinal and transverse centerlines, the longer dimension corresponding with the longitudinal direction). The portion of the specimen to be tested should only include the unitary absorbent member as defined by the specification. Therefore, the other materials that are not part of the absorbent member must be carefully removed such that the basis weight of the material is not impacted.

Procedure

The test apparatus is always zeroed before any measurements are taken. The weight of each sample is measured and recorded to the nearest 0.01 grams.

Calculations

The basis weight is calculated for each of the 3 specimens using the following equation:

$$\text{Sample Basis Weight(grams/meter}^2) = \frac{\text{Specimen Weight(grams)}}{0.01 \text{(meter}^2)}$$

Each of the samples is individually measured and the average of the samples is reported to the nearest 0.01 grams per square meter.

C. Bulk Density Calculation

The bulk density of a given sample is calculated according to the equation below using the caliper and basis weight measured for that given sample following the methods described above.

$$\text{Bulk Density(grams/centimeter}^3) = \frac{\text{Basis Weight(grams/meter}^2)}{\text{Caliper(millimeters)}} \div 1000$$

The bulk density for each of the samples is individually calculated and the average bulk density of the samples is reported to the nearest 0.01 grams per cubic centimeter.

D. Tensile Method

The MD and CD peak tensile are measured using a method based on Standard Test WSP 110.4 (05)—Option B, Standard Test Method for Breaking Force and Elongation of Nonwoven Materials (Strip Method), but with a shorter gauge length to enable measurements on finished products.

Apparatus

The apparatus necessary for the TENSILE METHOD consists of the following parts: 1) An MTS Synergie 400 (Model #SYN400) or equivalent with a constant-rate-of-extension of 100 mm/min; 2) A 100 N load cell (Model #SYN100) or equivalent, or a 500N load cell (Model #SYN 500) or equivalent for stiffer materials such as undeformed drylap.

Number and Preparation of Specimens

A minimum of eight representative samples are necessary, four for the MD tensile test and four for the CD tensile test. The specimen is cut from the center of the sample (e.g. centered on the intersection of the longitudinal and transverse centerlines). The portion of the specimen to be tested should only include the unitary absorbent member as defined by the specification. Therefore, the other materials that are not part of the absorbent member must be carefully removed such that the tensile strength of the material is not impacted. To prepare the samples for the MD tensile test, a specimen is die cut from each sample with a CD width of 50 mm and a MD length of 70 mm. For a sample that is being taken from a product, such as a feminine pad, the MD is assumed to represent the long direction of the pad and the CD is the direction orthogonal to the MD. To prepare the samples for the CD tensile test, a specimen is die cut from each sample with a MD length of 50 mm and a CD width of 50 mm.

Procedure

Standard Test WSP 110.4 (05)—Option B is followed with the following gauge length changes:
1. MD peak tensile: 50 mm gauge length
2. CD peak tensile: 30 mm gauge length Calculations The peak tensile is the maximum force reading for that specimen. Each specimen is measured individually and the average peak MD tensile and average peak CD tensile of the samples is reported to the nearest 0.1 N.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 grams" is intended to mean "about 40 grams".

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A bulked absorbent member having first and second surfaces, said absorbent member comprising at least one unitary absorbent fibrous wetlaid structure comprising at least some cellulose fibers, said absorbent member being partially stratified, and having a plurality of discrete deformations in said first surface wherein each of said deformations has a first end portion and a second end portion, and the first surface has first densified regions, wherein each of the first densified regions is adjacent to only the first end portion of each of said deformations, and each of said first densified regions has a plan view configuration that resembles a bow wave.

2. The bulked absorbent member of claim 1 having a bulk density between about 0.03 g/cm$^3$ and about 0.25 g/cm$^3$.

3. The bulked absorbent member of claim 1 further comprising an additional layer joined to said unitary absorbent fibrous wetlaid structure.

4. The bulked absorbent member of claim 1 wherein said absorbent member is partially stratified into strata that form alternating zones of high and low density through the thickness of the absorbent member.

5. The bulked absorbent member of claim 1 wherein said unitary absorbent fibrous wetlaid structure comprises at least about 98 wt. % cellulose fibers.

6. The bulked absorbent member of claim 1 wherein said unitary absorbent fibrous wetlaid structure comprises about 100 wt. % cellulose fibers.

7. The bulked absorbent member of claim 1, wherein each of said first densified regions has a plan view configuration that resembles a curvilinear bow wave.

8. The bulked absorbent member of claim 1, wherein within each of said first densified regions a portion of the bulked absorbent member is pushed up.

9. The bulked absorbent member of claim 1, wherein each of said deformations is a depression within the first surface.

10. The bulked absorbent member of claim 9, wherein each of depressions forms a corresponding protrusion from the second surface.

11. The bulked absorbent member of claim 1, wherein each of said deformations is an aperture.

12. The bulked absorbent member of claim 1, wherein:
each of the deformations is a first deformation;
each of the first densified regions has a plan view configuration that resembles a bow wave pointed in a first direction; and
the member has a plurality of second discrete deformations in said second surface wherein each of said second deformations has a first end portion and a second end portion, and the second surface has second densified regions, wherein each of the second densified regions is adjacent to only the second end portion of each of said second deformations, and each of said second densified regions has a plan view configuration that resembles a bow wave pointed in a second direction, which is opposite to the first direction.

13. The bulked absorbent member of claim 12 wherein the first deformations on the first surface of said absorbent member are in a consistent position relative to adjacent deformations of the second deformations on the second surface of the absorbent member and the first deformations form a consistent, repeating pattern.

14. The bulked absorbent member of claim 12 wherein the first deformations on the first surface of said absorbent member are in a varying position relative to adjacent deformations of the second deformations on the second surface of the absorbent member.

15. The bulked absorbent member of claim 12, wherein each of said second densified regions has a plan view configuration that resembles a curvilinear bow wave.

16. The bulked absorbent member of claim 12, wherein within each of said second densified regions a portion of the bulked absorbent member is pushed up.

17. The bulked absorbent member of claim 12, wherein each of said second deformations is a depression within the second surface.

18. The bulked absorbent member of claim 17, wherein each of the depressions forms a corresponding protrusion from the first surface.

19. The bulked absorbent member of claim 12, wherein each of said second deformations is an aperture.

* * * * *